(12) United States Patent
Tanghoej et al.

(10) Patent No.: US 9,775,965 B2
(45) Date of Patent: Oct. 3, 2017

(54) CATHETER WITH A BENDABLE ZONE

(71) Applicant: Coloplast A/S, Humlebaek (DK)

(72) Inventors: Allan Tanghoej, Kokkedal (DK); Lars Boegelund Jensen, Roedovre (DK)

(73) Assignee: Coloplast A/S, Humlebaek (DK)

( * ) Notice: Subject to any disclaimer, the term of this patent is extended or adjusted under 35 U.S.C. 154(b) by 52 days.

(21) Appl. No.: 14/598,234

(22) Filed: Jan. 16, 2015

(65) Prior Publication Data

US 2015/0182724 A1   Jul. 2, 2015

Related U.S. Application Data

(63) Continuation of application No. 12/698,241, filed on Feb. 2, 2010, now Pat. No. 8,986,286, which is a
(Continued)

(30) Foreign Application Priority Data

Jun. 29, 2001  (DK) ................................ 2001 01041
Sep. 24, 2001  (DK) ................................ 2001 01386
(Continued)

(51) Int. Cl.
*A61M 25/00* (2006.01)
*A61F 5/44* (2006.01)
*A61M 25/01* (2006.01)

(52) U.S. Cl.
CPC ........... *A61M 25/0054* (2013.01); *A61F 5/44* (2013.01); *A61M 25/002* (2013.01);
(Continued)

(58) Field of Classification Search
CPC .... A61F 5/44; A61F 5/453; A61F 2005/4402; B65B 69/0016; A61M 2018/00517;
(Continued)

(56) References Cited

U.S. PATENT DOCUMENTS 3,332,424 A * 7/1967 Minteer ............. A61M 25/0119
                                                              604/117
3,606,889 A * 9/1971 Arblaster ........... A61M 25/0111
                                                              206/364
(Continued)

OTHER PUBLICATIONS

Notice of Allowance dated Jul. 1, 2016, in U.S. Appl. No. 14/721,035.

*Primary Examiner* — Andrew Gilbert
(74) *Attorney, Agent, or Firm* — Coloplast Corp., Coloplast A/S; Nick Baumann

(57) ABSTRACT

A catheter insertable into a urethra to drain urine from a bladder includes a tubular portion, a sleeve disposed relative to the tubular portion, with the tubular portion having a bendable zone that is configured to allow the catheter to fold to a compact length. The catheter has a total catheter length measured between an end of a connector that is attachable to a drainage bag and an insertion end of the tubular portion that is insertable into the bladder. The compact length is less than the total catheter length, and the sleeve is operable to support the tubular portion by removing the bend in the bendable zone to thus align the connector axially with the insertion end of the tubular portion.

17 Claims, 32 Drawing Sheets

Related U.S. Application Data continuation of application No. 10/722,574, filed on Nov. 28, 2003, now Pat. No. 7,682,353, which is a continuation-in-part of application No. 10/184,081, filed on Jun. 28, 2002, now Pat. No. 8,066,693, which is a continuation-in-part of application No. 10/026,819, filed on Dec. 27, 2001, now Pat. No. 7,311,698, which is a continuation-in-part of application No. 09/893,514, filed on Jun. 29, 2001, now abandoned.

(30) Foreign Application Priority Data

| Dec. 13, 2001 | (DK) | 2001 01869 |
| Dec. 13, 2001 | (DK) | 2001 01870 |
| Apr. 17, 2002 | (DK) | 2002 00569 |
| Apr. 17, 2002 | (DK) | 2002 00570 |
| Jun. 13, 2002 | (DK) | 2002 00895 |

(52) U.S. Cl.
CPC .... *A61M 25/0009* (2013.01); *A61M 25/0017* (2013.01); *A61M 25/0023* (2013.01); *A61M 25/0067* (2013.01); *A61M 25/01* (2013.01); A61M 2025/0025 (2013.01); A61M 2025/0175 (2013.01); A61M 2202/0496 (2013.01); A61M 2205/04 (2013.01)

(58) Field of Classification Search
CPC .............. A61M 25/0017; A61M 25/01; A61M 25/002; A61M 2025/0175; A61M 2025/0034; A61M 2025/0062; A61M 2210/1078; A61M 2210/1085; A61M 2210/1089; A61M 2210/1096
See application file for complete search history.

(56) References Cited

U.S. PATENT DOCUMENTS

| 3,642,004 | A | * | 2/1972 | Osthagen | A61M 25/0075 128/DIG. 25 |
| 3,750,875 | A | * | 8/1973 | Juster | A61M 25/002 206/364 |
| 3,782,381 | A | * | 1/1974 | Winnie | A61M 25/0606 604/164.09 |
| 4,361,148 | A | * | 11/1982 | Shackleford | A61J 1/10 604/410 |
| 4,500,313 | A | * | 2/1985 | Young | A61B 5/1076 600/587 |
| 4,601,713 | A | * | 7/1986 | Fuqua | A61M 25/0023 604/103.14 |
| 4,871,358 | A | * | 10/1989 | Gold | A61M 25/0119 604/271 |
| 5,183,470 | A | * | 2/1993 | Wettermann | A61B 17/3415 604/158 |
| 5,290,229 | A | * | 3/1994 | Paskar | A61M 25/0041 600/434 |
| 5,591,132 | A | * | 1/1997 | Carrie | A61B 17/3401 604/158 |
| 5,653,700 | A | * | 8/1997 | Byrne | A61M 25/01 604/328 |
| 5,681,274 | A | * | 10/1997 | Perkins | A61M 27/008 604/264 |
| 6,010,479 | A | * | 1/2000 | Dimitri | A61J 15/0015 604/525 |
| 6,019,753 | A | * | 2/2000 | Pagan | A61M 16/04 604/523 |
| 6,146,381 | A | * | 11/2000 | Bowe | A61M 25/0041 600/374 |
| 6,355,004 | B1 | * | 3/2002 | Pedersen | A61F 5/44 600/581 |
| 6,358,229 | B1 | * | 3/2002 | Tihon | A61M 25/0017 604/164.01 |
| 6,544,240 | B1 | * | 4/2003 | Borodulin | A61M 25/01 604/329 |
| 6,610,005 | B1 | * | 8/2003 | Tao | A61B 17/435 600/33 |
| 9,067,039 | B2 | | 6/2015 | Tanghoej et al. | |
| 2001/0039413 | A1 | * | 11/2001 | Bowe | A61M 25/0041 604/532 |
| 2003/0018302 | A1 | | 1/2003 | Kavanagh et al. | |
| 2003/0032944 | A1 | * | 2/2003 | Cawood | A61F 5/4405 604/544 |
| 2003/0199849 | A1 | * | 10/2003 | Hackett | A61M 25/0069 604/523 |

\* cited by examiner

CATHETER WITH A BENDABLE ZONE

FIELD OF THE INVENTION

The present invention relates to an elongated tubular catheter member for draining bodily fluids, e.g. from the bladder.

BACKGROUND OF THE INVENTION

Catheters for draining the bladder are increasingly used for intermittent as well as indwelling or permanent catheterisation. Typically catheters are used by patients suffering from urinary incontinence or by disabled individuals like para- or tetraplegics who may have no control permitting voluntary urination and for whom catheterisation may be the way of urinating.

Catheterisation is thus increasingly becoming a daily-life procedure significantly improving quality of life for a large group of patients.

Typically, catheters are designed for one-time use and accordingly the costs for producing, packing and sterilising a catheter is an important issue. Existing catheters are made from a single piece of a continuous catheter tube. Typically, the thickness of the catheter tube is constant throughout its length.

The length of the catheter enables insertion of a certain length into the urethra until urine starts to flow. At this point, a certain over-length of the catheter should be available. The over-length supports for the user to firmly hold the catheter and to guide the urine to a place of disposal and to withdraw the catheter safely and without any risk of the catheter disappearing into the urethra.

Existing catheters are designed to minimise the risk of sores in the mucous membrane and to give substantially no sensation of pain during insertion. Accordingly known catheters are typically provided with a smooth and slippery surface optimised for safe and comfortable insertion into the urethra. Therefore, it may often be difficult, not least for the disabled user, to handle the catheter by manipulation of the slippery over-length.

It is often important that the tubular member does not collapse or kink and thereby blocks the passage for the urine to drain through the catheter. Existing catheters are therefore typically made from a form stabile and relatively hard but still bendable tube e.g. made from PVC, PU or PE. Since the hardness of the tubes is selected relatively high with the view to avoid kinking, the catheters may collapse if they are bend with a too small radius of curvature.

Accordingly, existing catheters not only have a considerable length but they are also typically packed in an elongate condition. Therefore the existing catheters may be troublesome to handle and to bring along, not least for the individuals for whom catheterisation is a daily-life procedure, wherein catheterisation takes place several times a day and wherein the used catheters must be disposed via the garbage collection.

DESCRIPTION OF THE INVENTION

It is an object of preferred embodiments of the present invention to overcome the above described disadvantages of the known catheters.

Accordingly, the invention provides a kit for preparing a catheter for draining a human bladder, the kit comprising at least two catheter sections defining a longitudinally extending passage therein, the sections being arranged in a coextending fashion with a tubular protective member surrounding a first, proximal one of said catheter sections, the kit further comprising a joint for interconnecting the first and the second catheter section, the joint defining a substantially liquid tight seal at a distal end of a substantially annular and longitudinally extending cavity provided between the proximal end portion of the first catheter section and an inner wall of the tubular protective member, the tubular protective member being removably connected to the joint and/or to the second catheter section, so that, when the tubular protective member is removed, a proximal end portion of the first catheter section is exposed and ready for insertion into the human urethra.

In particular, the catheter may be provided so that the sections are adapted to be moved between at least two positions with respect to each other. One position being a position wherein the second section surrounds the first section and the other position being a position wherein the second section forms an extension for the first section.

The joint between the first section and the second section may be a telescopical joint providing a liquid tight seal between the sections while they are moved between the first position and the second position. As an example, the first section may be provided with a piston seal adapted to slide along the inner surface of the second section while the first section is being pulled out of second section between the first and second position.

In order to allow the user to insert the first section into a body canal, a locking arrangement of may be provided for locking the position of the first section with respect to the second section, when the sections are in the second position, i.e. when the catheter is in a configuration ready for insertion into the body canal.

In order to allow the user to pull the first catheter section out of the second catheter section without touching the insertable part of the catheter, the tubular protective member may preferably be provided to engage the first catheter section in a locking engagement. Thereby, it will be allowed to use the tubular protective member to pull the first catheter section out of the second catheter section.

When the first catheter section has been pulled out of the first catheter section, i.e. when the sections are in the second position, i.e. in the position wherein the second catheter section forms an extension for the first catheter section, the tubular protective member should be allowed to disengage the first catheter section. When the tubular protective member has been removed, the catheter is in a "ready to insert" state.

In order to use the second catheter section as a sealing envelope or package for the first catheter section, i.e. for the insertable catheter section, the distal end of the first catheter section may preferably be adapted to seal an opening in a distal end of the second catheter section while the sections are in the first position and not to seal set opening when the sections are in the second position. When the sections are brought into the second position, i.e. when the catheter is "ready for insertion", the opening in the distal end of the second section may be used for draining the bodily liquids, e.g. urine out of the catheter.

In order to allow the annular cavity to be used e.g. for carrying a frictional reducing substance, e.g. a water or saline solution for a hydrophilic catheter, a hydrogel or similar lubricating substance, the kit may preferably be provided with a sealing engagement between the tubular protective member and the first catheter section when the tubular protective member is engaging the first catheter section. When the tubular protective member is disengaged from the first catheter section, i.e. after the catheter has reached its "ready for insertion state", the annular cavity is open to the ambient atmosphere thus exposing the insertable tip of the first catheter section and allowing the user to drain surplus friction reducing substances.

In one embodiment, the first catheter section is provided with a hydrophilic surface and the friction reducing substance provided in the annular cavity is a liquid swelling medium, e.g. water or a saline solution.

The catheter sections could be provided in the form of oblong tubular, hollow sections wherein the passage is defined inside the sections or the sections may comprise an oblong solid kernel with one or more vanes extending radially from the kernel and along the entire length thereof. The vanes thus defines a number of draining passages for draining urine between the kernel and a bodily draining passage, e.g. the urethra. The advantage of using a passage defined between a solid kernel and a wall of the urethra is that the flow of bodily fluid cleans the urethra and thus reduces the risk of infection compared with a traditional catheter, wherein the bodily fluid is drained inside the catheter isolated from the body canal.

A rigidity of substantially the full length of the catheter allows for manipulation of the catheter as one uniform catheter tube. Thereby, insertion of the proximal end of the catheter may be performed without touching the part of the catheter which is going to be inserted into the urethra. Preferably the catheter is provided with a bending moment defined as the product between E-modulus and moment of inertia of at least 1 MPamm$^4$ Since the proximal (inserted) end of the catheter, for male individuals, must pass prostate in a curved passage, the proximal end portion of the catheter, e.g. the first 10-50 mm., such as 20-40 mm., such as 25-35 mm, such as the first 30 mm. of the catheter may be provided with an even lower bending moment defined as the product between E-modulus and moment of inertia of less than e.g. 0.6 MPamm$^4$ or even less than 0.3 MPamm$^4$. Other parts of the catheter, e.g. a distal end portion where the urine is drained into the lavatory, a bag or similar place of disposal, may similarly be provided with a reduced bending moment.

The cross-sectional flow area or the hydraulic radius defined as the ratio of the cross-sectional flow area to the wetted perimeter, may be selected independently upon the length, e.g. on the basis of the size of the urethra, which size depends on the individual using the catheter. Each of the sections may have either the same cross-sectional flow area or hydraulic radius or each section may have individual cross-sectional flow areas or hydraulic radiuses. However, at least one part of one section should have a cross-sectional shape and size adapted for the size of urethra or an artificial urinary canal. Similarly one section should preferably have a length selected on the basis of the length of the urethra or the urinary canal. Thereby it may be achieved that only one section is to be inserted and therefore no transition between sections needs to be inserted. However, especially for male individuals where urethra is particularly long, a catheter having an inserted length divided in two sections or more may be provided. In this specific case it will be appropriate to provide a transition between the sections which at least on the outer surface of the catheter have substantially no recess or sharp edge.

At least one of the catheter sections may be provided in a length in the range of 50-90 mm, such as in the range of 55-85 mm, such as in the range of 60-80 mm, such as with a length in the size of 70 mm, which length has been found to be a suitable insertable length for most female individuals. For male individuals, catheter sections may be provided in a length in the range of 180-250 mm, such as in the range of 190-240 mm, such as in the range of 200-230 mm such as in the size of 220 mm. For the male individuals it may further be preferred to provide at least a part of the inserted end of the catheter in a material or in dimensions so that a the tube becomes very flexible, without kinking. This will ease the passage of the catheter past prostate.

The outer cross-sectional shape of at least one of the sections should preferably be substantially circular with a cross-sectional area in the range of 0.5 mm$^2$–30 mm$^2$.

Even more preferred is to provide at least one of the sections with a hydraulic radius ("cross-sectional area"/ "circumferential length") in the size of 0.2-1.5 mm. Alternatively, at least one of the sections should have a cross-sectional shape matching the shape of urethra or an artificial urinary canal, still with a cross-sectional area in the range of 0.5 mm$^2$–30 mm$^2$ or a hydraulic radius in the size of 0.2-1.5 mm. However, the other of the sections does not necessarily have to have the same cross-sectional shape, nor the same hydraulic radius. The wall thickness of the catheter should preferably be in the range between 0.5-1.5 mm.

The catheter or at least a part of the catheter could be made from a thermoplastic elastomeric material, other thermoplastic materials, curable elastomeric materials, polyamide resins or elastomers or any mixture thereof, i.e. the group may comprise materials like, PVC, PU, PE, latex, and/or Kraton™.

In one embodiment, the catheter may be divided in separate catheter sections. Each catheter section has at least one end provided with means for connecting the section with another section corresponding to an adjacent part of the catheter. As an example the catheter may be divided into two tubular connectable pieces connected by connecting means.

Preferably, the connecting means are provided with a rigidity allowing for manipulation of at least one of the catheter sections by manipulation of one of the other catheter sections. At least the connection between each of the pieces should provide sufficient rigidity to allow one proximal section to be inserted into the urethra by manipulation of one of the other sections.

Therefore, the connection is preferably provided so that at least the part of the catheter extending the connection zone, has a bending moment defined as the product between E-modulus and moment of inertia of at least 0.6 MPamm$^4$ such as at least 1 MPamm$^4$ In order not to have the individual sections falling apart during use, the connection should preferably be adapted to take up an axial force of at least 0.5 Newton or at least to take up an axial force larger than the axial force required for withdrawal of the catheter from the urethra or artificial urinary canal.

The pieces may be connected e.g. telescopically or via a hinge enabling one of two sections to rotate in relation to the other of the two sections. It is appreciated that the sections are in fixed engagement so that they do not disconnect during use of the catheter, while urine is drained through the catheter. However, since the urine is always drained in one direction, the connection does not necessarily have to be liquid-tight. As an example a telescopic connection may be established by inserting the section adapted for insertion into urethra into a distal section. The flow direction of the urine will at least substantially prevent the connection from leaking even though the connection as such is not completely liquid tight.

However, a completely sealed connection may provide an even safer catheter with a reduced risk of contaminating hands etc.

In one embodiment wherein the two catheter sections are arranged in a telescopic fashion, the first catheter section may be intended for insertion into the human urethra, whereas the second catheter section is usually intended for forming a prolongation of the catheter outside the human urethra during use of the catheter. In use, that is in the second mutual configuration of the two catheter sections, the second catheter section preferably coextends with the first catheter section away from a distal end of the first catheter section. In the first mutual configuration, which usually is the configuration in which the telescopic kit is stored and transported, at least a portion of the first catheter section may be surrounded by the second catheter section. In the first mutual configuration, the tubular protective member is provided between an outer surface of the first catheter section and an inner wall of the second catheter section. The dimensions of the tubular protective member and the catheter sections may be such that, in the second mutual configuration, a substantially annular and longitudinally extending cavity is formed between an outer surface of the first catheter section and an inner wall of the second catheter section. The first catheter section may have a hydrophilic surface, and a liquid swelling medium may be provided in the annular cavity, so as to swell the hydrophilic surface of the first catheter section, whereby the first catheter section being encapsulated in the tightly sealed annular cavity may be preserved in its wet, swelled condition for a period of 1-5 years, such as 3-5 years, or more. A tight sealing of the annular cavity is desired for all kinds of catheter surfaces, including hydrophilic and hydrophobic catheter surfaces, in order to prevent contamination to enter into the cavity. Thus, in the first mutual condition, the telescopical joint may serve to define a liquid and contamination tight seal between the second catheter section and an ambient atmosphere.

A distal end of the second catheter section is preferably provided with a tight seal which may be tight to both liquids and contamination, and which may be removable, so that when a distal end of the second catheter section is inserted into, e.g., a urine collection bag, a passage for urine is formed at the location from which the seal has been removed. The tubular protective member is preferably removable when the first and second catheter sections are in the second mutual position, so that, when the tubular protective member is removed, the proximal end portion of the first catheter section is exposed and ready for insertion into the human urethra. The distal end of the second catheter section may as an alternative be provided into one piece with a collection bag. As an example, the second catheter section may be provided with a plastic welding-flange for adhesively bonding a plastic collection bag to the second catheter section.

According to another preferred embodiment, the catheter may comprise at least two sections not being separated but being divided by a bendable zone. The bendable zone could e.g. be a bellow shaped section or the zone could be an area wherein the thickness of the tubular material is smaller and wherein the zone accordingly has a lower bending moment. The zone could e.g. be provided in a more resilient or flexible material allowing for bending the catheter tube without kinking or damaging the tube.

In general, the problems of introducing a catheter into urethra depend not only of the size of the introduced part of the catheter but also on the slipperiness of the introduced part. The catheter section or at least a part of the catheter section or sections adapted for insertion into urethra or an artificial urinary canal may provide a surface slipperiness for easy and safe insertion. However, it has been found that lubricated or slippery surfaces, are difficult to handle, not least for a user having reduced dexterity. It is therefore an object of the present invention to provide a catheter with an inserted part being treated so as to provide a slippery surface and another part not being treated, so as to provide a surface which may easily be handled. The division of the catheter into one part being treated and one part not being treated may preferably follow the aforementioned division of the catheter with the purpose of making the catheter collapsible or separable. According to an alternative embodiment, the parts may be provided in the form of one part being smooth and another part being provided with a rough surface.

According to a preferred embodiment, at least one of the sections is provided with gripping means easing a firm grip in the catheter. Not least for the disabled user, the gripping means will improve the value of the catheter considerably. Gripping means may be provided as a radially extending flange or flanges or as a zone having a large outer cross sectional diameter. The catheter, or at least one of the catheter sections, may also be provided with means for engaging an external handle. As an example, one of the tubular catheter tubes may be provided with a ring-shaped bulge for attaching a handle. The ring-shaped bulge could be provided as a short tubular piece of plastic with a larger radial size than the catheter, the catheter being inserted and glued into the short piece of plastic.

A section provided with a hydrophilic surface treated with a liquid swelling medium may provide an excellent lubrication for the insertion and also provide compatibility with the body tissue. It is therefore a further preferred embodiment of the invention to provide at least one of the sections with a hydrophilic surface layer.

One of the catheter sections could be used as a sterile package for the other sections, e.g. by arranging the sections in a telescopic manner inside one section, closing and sealing that section in both ends, e.g. by a peelable and optionally a metallised foil e.g. made from a thermoplastic elastomeric material, other thermoplastic materials, curable elastomeric materials, polyamide resins or elastomers or any mixture thereof, i.e. the group may comprise materials like, PVC, PU, PE, latex, and/or Kraton™, thereby allowing for sterilising the assembly by radiation.

The liquid swelling medium for the hydrophilic surface may be provided in the package for initiation of the low friction character already when the catheter is being packed. The liquid swelling medium may simply be a saline solution, a bactericidal solution capable of swelling the hydrophilic surface and capable of keeping the surface in a sterile condition or it may be pure water. The swelling may also be initiated already before packaging of the catheter, the catheter then being packed in a substantially gas impermeable package for conservation of the moistened surface. Furthermore, the liquid swelling medium may be provided in a capsule or container packed together with the catheter for swelling of the hydrophilic material immediately prior to the insertion.

According to another aspect the present invention relates to a bendable urinary catheter for draining a human bladder comprising:
 a flexible elongated tube with an inner cross-sectional shape and size defining a first conduit for draining urine, said tube having an insertion end and a discharge end, and
 a supporting member being introduced into the first conduit and provided with an outer cross-sectional shape and radial size substantially equal to the inner cross-sectional shape and size of the elongate tube so as to support said tube against collapsing during bending of the tube, the supporting member having a flexibility allowing curling.

The discussion set forth above in connection with the features of embodiments wherein the first and second catheter sections are arranged in a telescopic fashion also apply to the kit aspects of the invention. Thus, embodiments of the kit may be regarded as modifications of telescopic embodiments of the kit, the modification comprising that a longitudinal movement of the two catheter sections relative to each other is usually not intended and that only one mutual configuration is usually intended. Further, all elements and features discussed above may be provided in the kit, to the extent that such features and elements are appropriate in the catheter.

With the catheter there may be provided a supporting member for being introduced into a first conduit of the catheter, the conduit being for draining urine, the supporting member being provided with an outer cross-sectional shape and radial size substantially equal to the inner cross-sectional shape and size of the elongate tube so as to support said tube against collapsing during bending of the tube, the supporting member having a flexibility allowing curling.

The flexible elongated tube could have the shape of a regular catheter of the known kind. Preferably, the tube or at least a part of the tube is made from a thermoplastic elastomeric material, other thermoplastic materials, curable elastomeric materials, polyamide resins or elastomers or any mixture thereof, i.e. the group may comprise materials like, PVC, PU, PE, latex, and/or Kraton™.

The supporting member supports the catheter to avoid collapsing when the catheter is bend, e.g. for the purpose of packing the catheter in user friendly short packages. The supporting member may be either solid or the supporting member may be hollow and thus defining a second conduit. The solid supporting member should be adapted for removal prior to draining of the bladder, whereas a hollow supporting member may remain inside the tube while the bladder is emptied through the first and second conduit.

The supporting member may as an example be glued inside the elongated tube or the supporting member may even be moulded into the tube during the process of producing the tube. The supporting member may even be completely integrated in the elongated tube.

The supporting member could be made from any suitable material such as e.g. plastic, steel, aluminium, a thermoplastic elastomeric material, other thermoplastic materials, curable elastomeric materials, polyamide resins or elastomers or any mixture thereof. As an example, the supporting member may be a helical spring provided in a length in the range of 20-60 mm, such as in the range of 30-50 mm, such as in the range of 35-45 mm. The spring should be positioned inside the elongated tube in the zone where it is desired to bend the catheter, e.g. midway along the longitudinal axis of the elongated tube. During use, the urine is drained through the first conduit of the elongated tube and past the supporting member through the second conduit.

In one embodiment, the supporting member is provided in a length in the range of 60-120 mm, such as in the range of 70-110 mm, such as in the range of 80-100 mm. and the supporting member may even be extending out of the discharge end of the elongated tube. This will enable the user to remove the supporting member during the process of inserting the catheter into urethra.

The supporting member may be provided with gripping means for easing withdrawal of the supporting member from the discharge end during insertion of the catheter.

A method for producing a urinary catheter comprising a proximal insertion section defining an inner elongated passage for urine, and at least one opening near a proximal end of the proximal insertion section for allowing urine to pass from the human bladder into the inner elongated passage, may comprise the steps of:
providing a mould, defining the shape of at least the proximal insertion section,
forming the proximal insertion section by injection moulding,
removing the proximal insertion section from the mould.

Whereas longitudinally extending catheters made from plastics materials have hitherto been manufactured by a relatively costly process involving extruding the catheter body, forming a rounded tip thereof by heat treatment, cutting transversely extending passages for urine near the tip of the catheter by means of a cutting tool, and rounding edges of the transversely extending passages by heat treatment, the method according to the fourth aspect of the invention has the advantage that it allows for a more efficient and more accurate controllable manufacturing process with less waste of material and fewer production steps.

The catheter may further comprise a connector part for connecting the proximal insertion section to a further catheter section or to a urinary collection bag. The connector part may be made from the same material as the proximal insertion section, whereby, at the step of forming the proximal insertion section, the proximal insertion section and the connector part may be formed substantially simultaneously. Alternatively, the connector part may be made from a material different from the material of the proximal insertion section, whereby the connector part and the proximal insertion section are formed in distinct process steps, for example in a multi-component injection moulding process.

BRIEF DESCRIPTION OF THE DRAWINGS

Preferred embodiments of the invention will now be described in details with reference to the drawing in which.

DETAILED DESCRIPTION OF THE DRAWINGS

Section I

Figure 1:
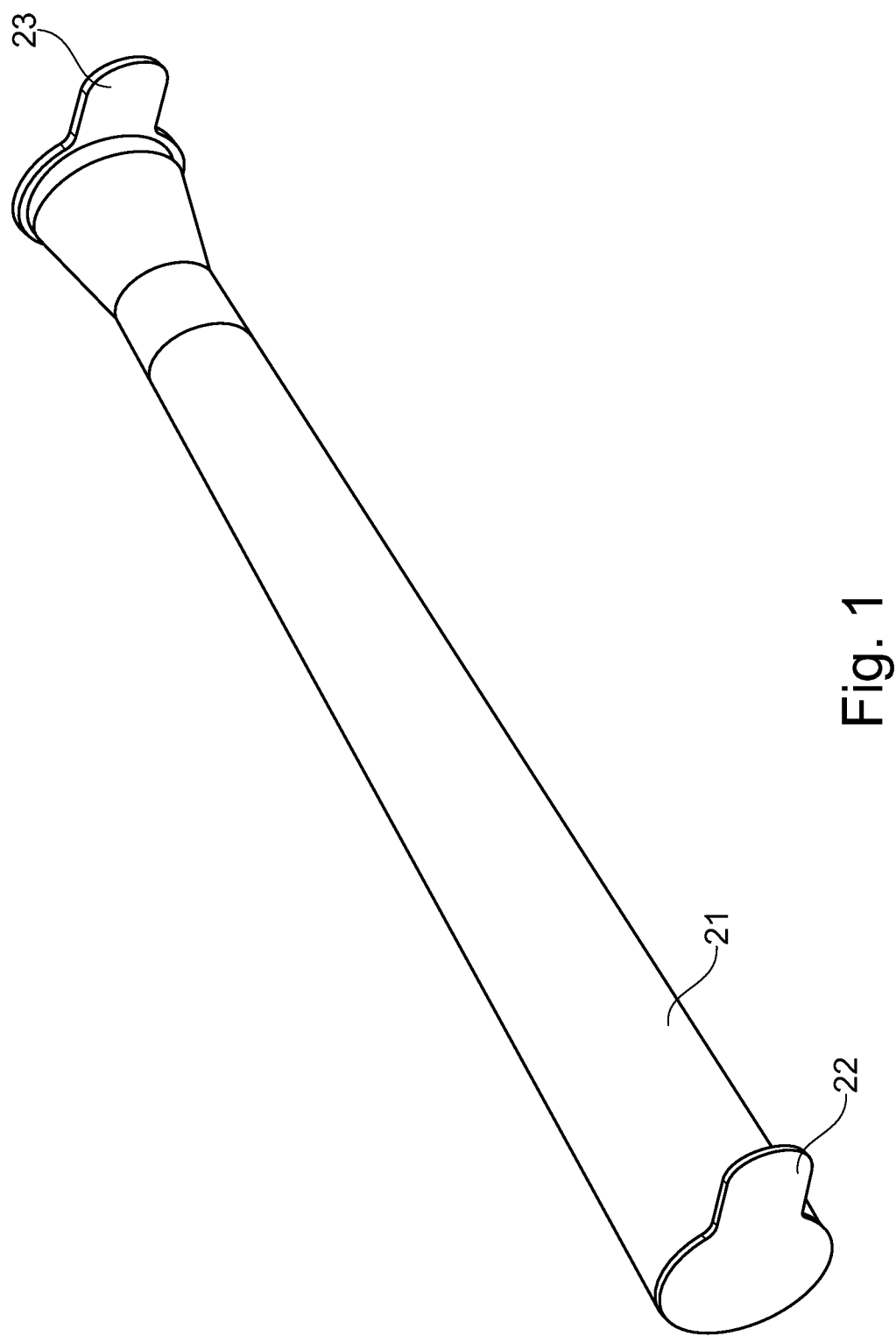
FIG. 1 shows an embodiment of the kit, wherein one catheter part is inserted for storage into another of the catheter parts thus substituting a catheter package.

FIG. 1 shows an embodiment of the catheter kit according to the present invention, wherein the first catheter section, not shown in FIG. 1, is sterilely packed inside the second catheter section 21, the second catheter section being sealed in both ends with sealing caps or foils 22, 23.

Preferably the first section is coated with a hydrophilic coating, providing a low friction surface of the first catheter section when treated with a liquid swelling medium. The coating could be of the kind which sustains being activated with the liquid swelling medium for longer time, e.g. for several month. Thereby the liquid swelling medium could be provided in the catheter package from the time of packaging so as to provide a ready-to-use catheter. Hydrophilic coatings are known per se, see e.g. the published patent applications WO 98/58988, WO 98/58989, WO 98/58990 or EP 0570370. For this purpose, the sealing caps or foils should preferably be provided in a gas impermeable material for conservation of the humidity and thus the lubricity of the catheter for longer time, e.g. for several month. As an example, the second catheter section and/or the sealing caps may be made from a thermoplastic elastomeric material, other thermoplastic materials, curable elastomeric materials, polyamide resins or elastomers or any mixture thereof, i.e. the group may comprise materials like, PVC, PU, PE, latex, and/or Kraton™. The caps may be provided with a thickness allowing for sufficient gas impermeability. As an alternative, they may be made from metallised foils.

Figure 2:
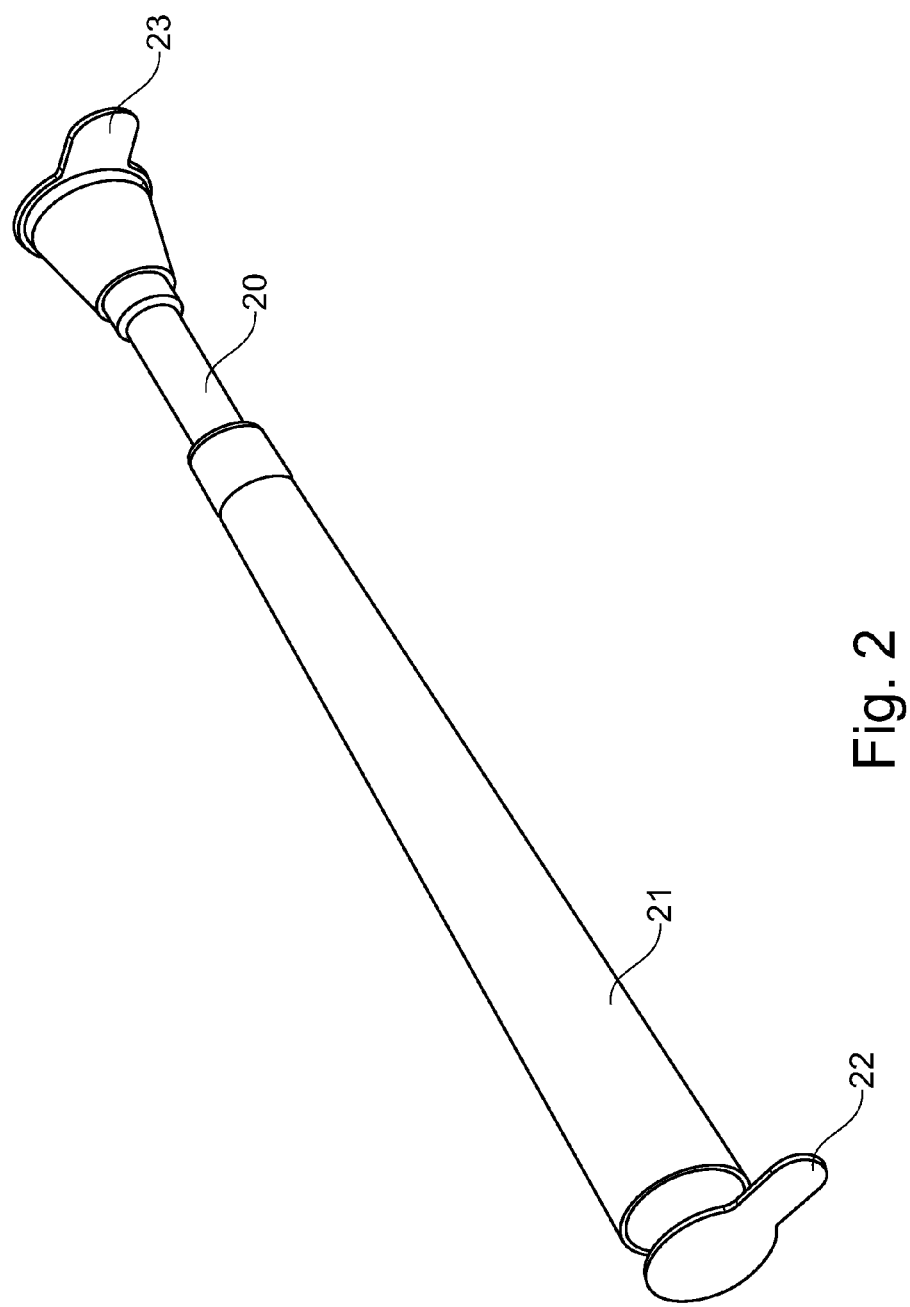
FIG. 2 shows the embodiment of FIG. 1, wherein the inserted catheter part is partially withdrawn from one end of the package.

As seen in FIG. 2, the first catheter section is easily withdrawn from the second catheter section by pulling the cap or foil 23 which cap or foil engages the distal end of the first catheter section.

Figure 3:
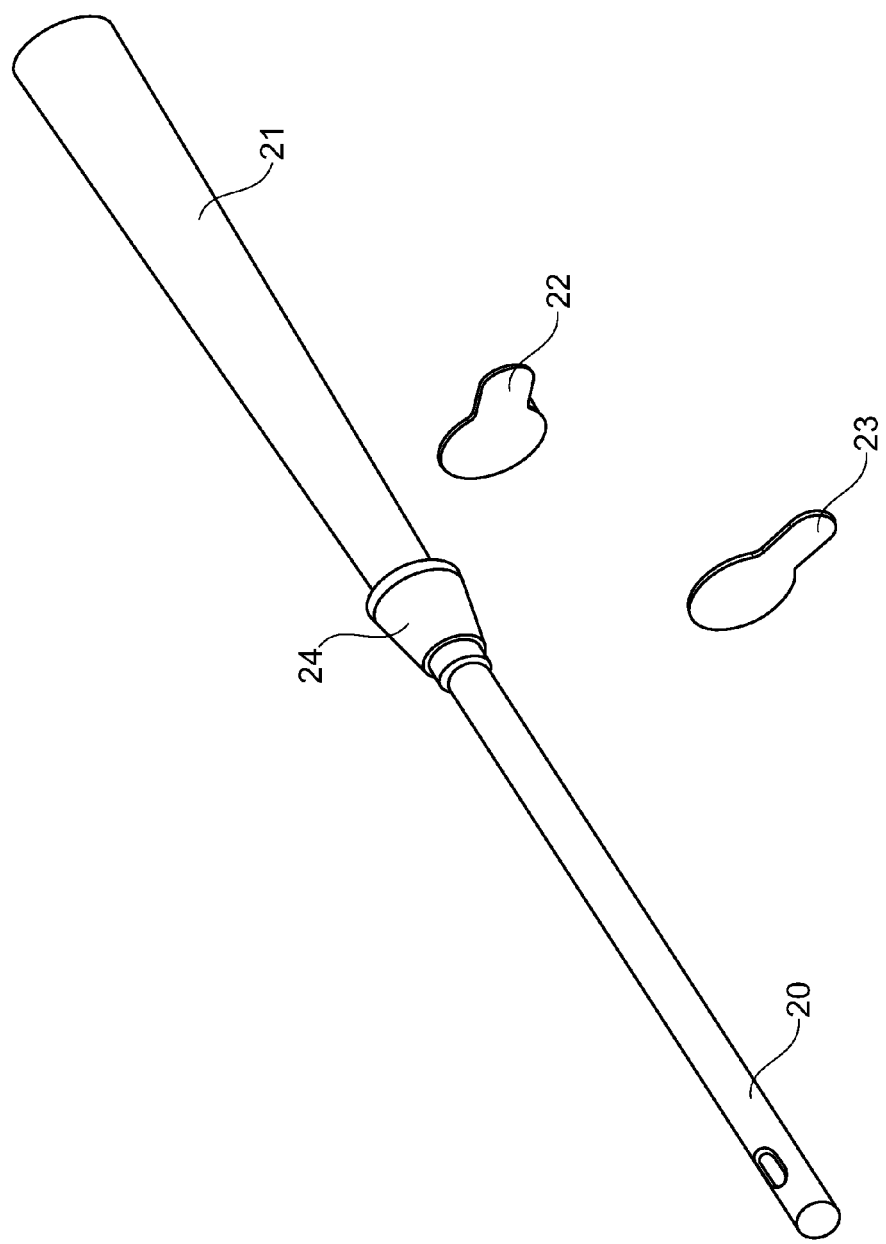
FIG. 3 shows the embodiment of FIGS. 1 and 2, wherein the inserted catheter part is completely withdrawn from the package and then attached to the other end of the package, the package thus functions as a handle for manipulation of the catheter.

FIG. 3 shows the assembled catheter after the first catheter section has been attached to the second catheter section. The foil or cap 23 can either be removed completely as shown in FIG. 9 or can at least be penetrated by the connecting means 24 of the second catheter section.

FIGS. 4-7 illustrate an embodiment of a catheter kit wherein the first and second sections 42, 44 are telescopically interconnected. A tubular protective member 46 surrounds a portion of the first catheter section 42 and forms a substantially annular cavity 48 around the first catheter section. In the second mutual configuration, shown in FIG. 16, in which the kit is intended to be stored and shipped, the first catheter section 42 and the tubular protective member 46 are inserted as far as possible into the second catheter section 44. A hydrophilic swelling medium, such as water, may be provided in the cavity 48, so that a hydrophilic surface coating optionally provided at the surface of the first catheter section 48 is stored in its swelled, i.e. wet condition. A surplus of hydrophilic swelling medium may be present in the cavity 48 in order to prevent the hydrophilic surface coating from drying out. A liquid-tight seal 50 is provided at the distal end of the first catheter section 42. A liquid-tight closing member 52 closes the distal end of the second catheter section 44. In one embodiment, the closing member 52 is removable so that a passage is provided between the second catheter section 44 and a urine collection bag, or another device for accumulating or conveying urine, mounted to the distal end of the section catheter section 44, when the closing member 52 is removed. In another embodiment, the closing member 52 is an integrated part of the second catheter section 44, in which case a wall 53 of the closing member 52 may be perforated in order to provide a passage between the second catheter section 44 and a urine collection bag, or other device for accumulating or conveying urine, mounted to the distal end of the section catheter section 44. In yet another embodiment, the closing member 52 may be substituted by a perforated end wall, e.g. a wall made from a central plate connected to the outer wall of the second catheter section 44 at its distal end by means of radially extending ribs or spokes. In such an embodiment, the first catheter section 42 and the seal 50 may be formed as a single, integrated piece.

Figure 4:
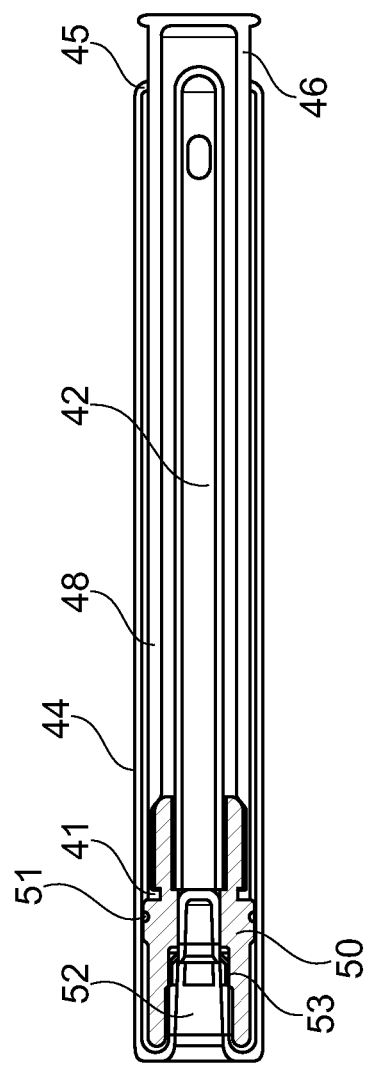
FIGS. 4-7 illustrate an embodiment of a kit according to the invention, wherein the catheter sections are arranged in a telescopic fashion.
Figure 5:
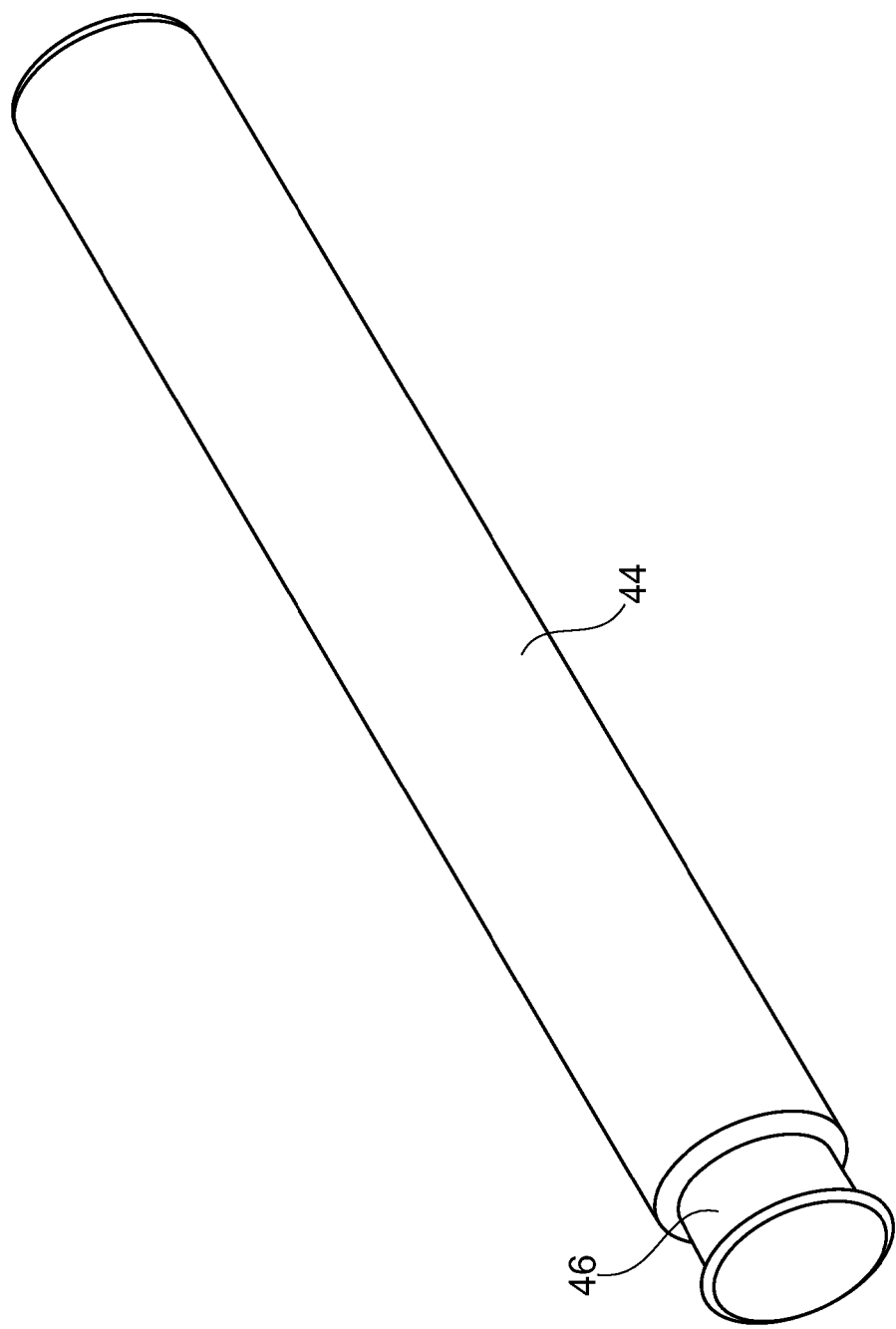
Figure 6:
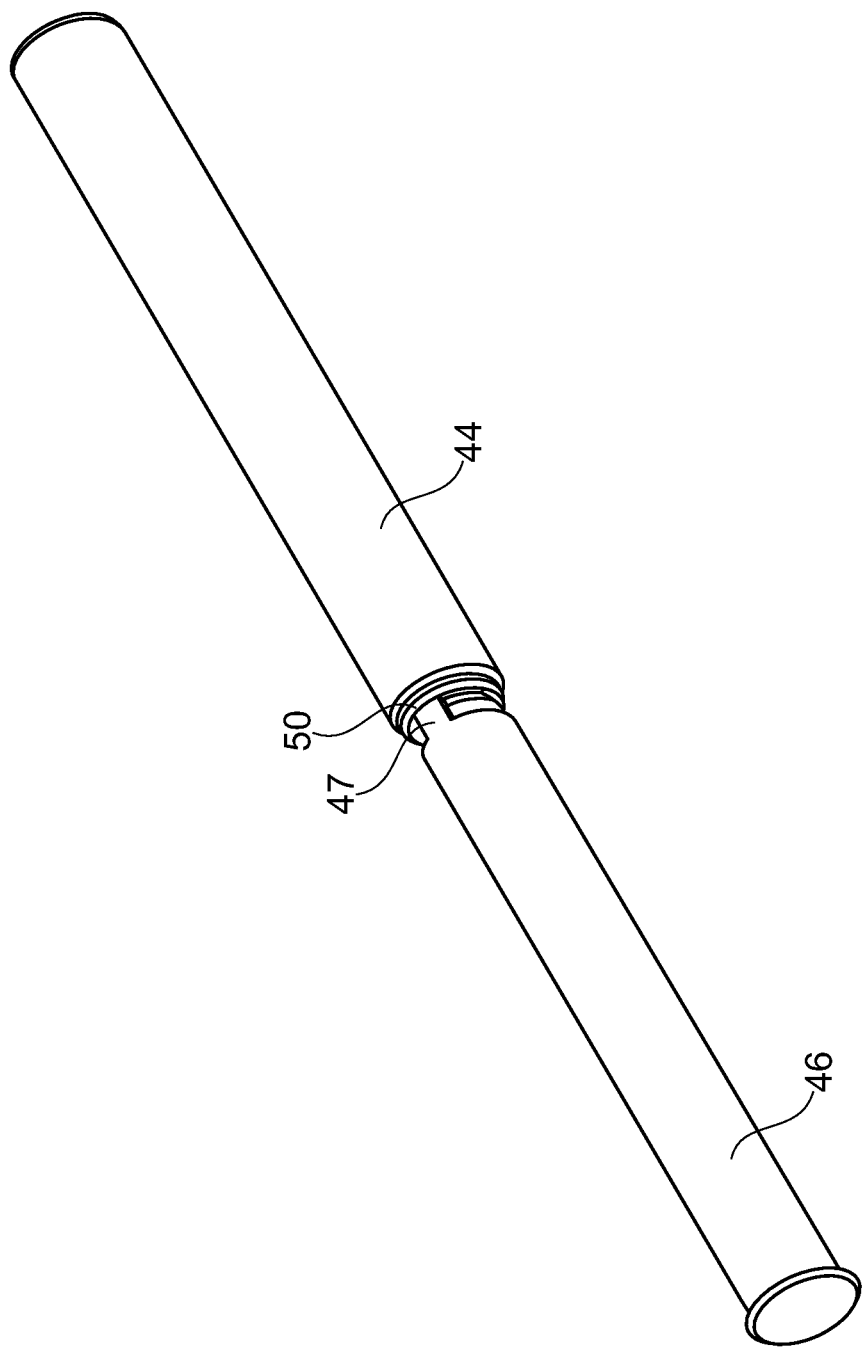
Figure 7:
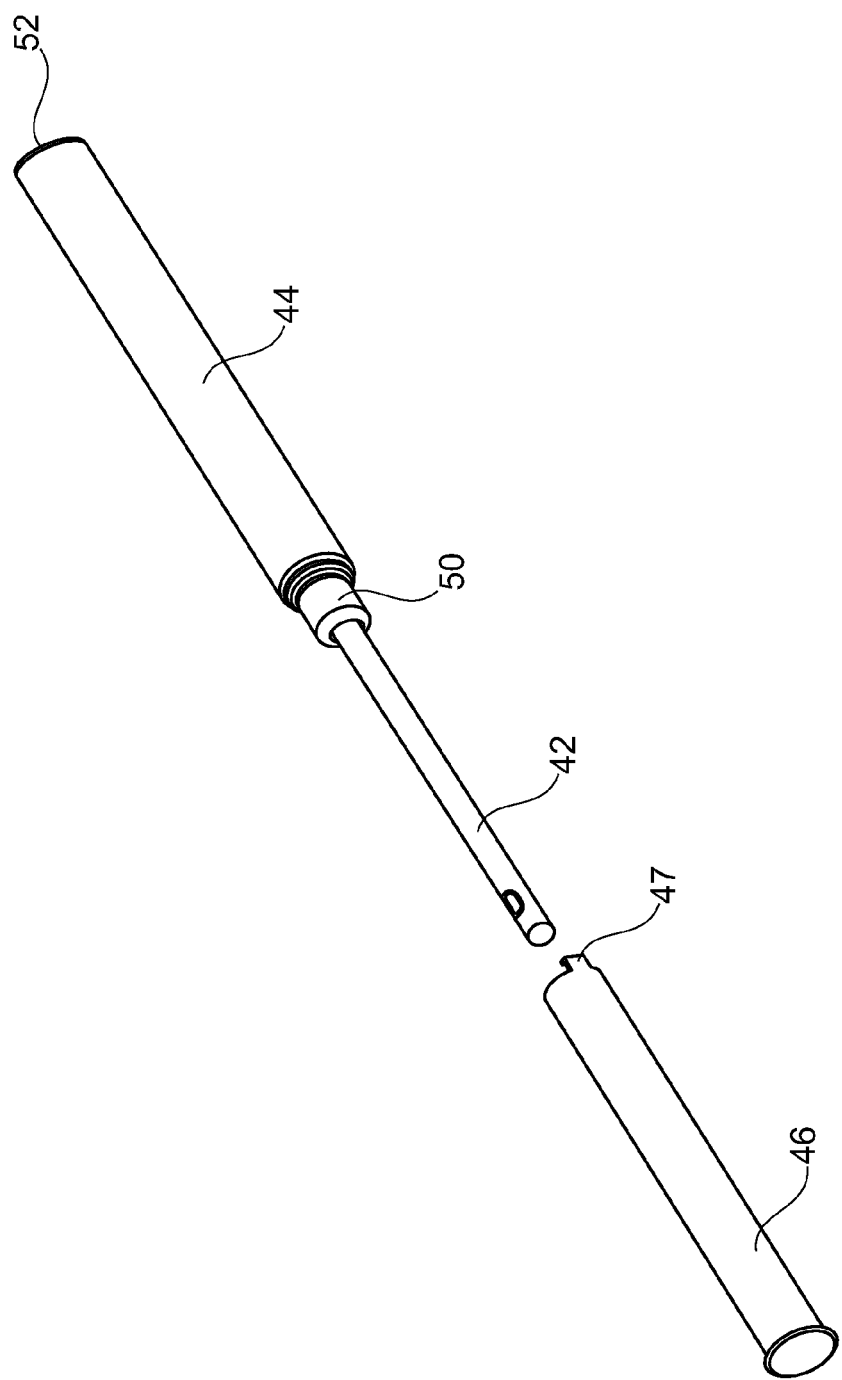
Figure 8:
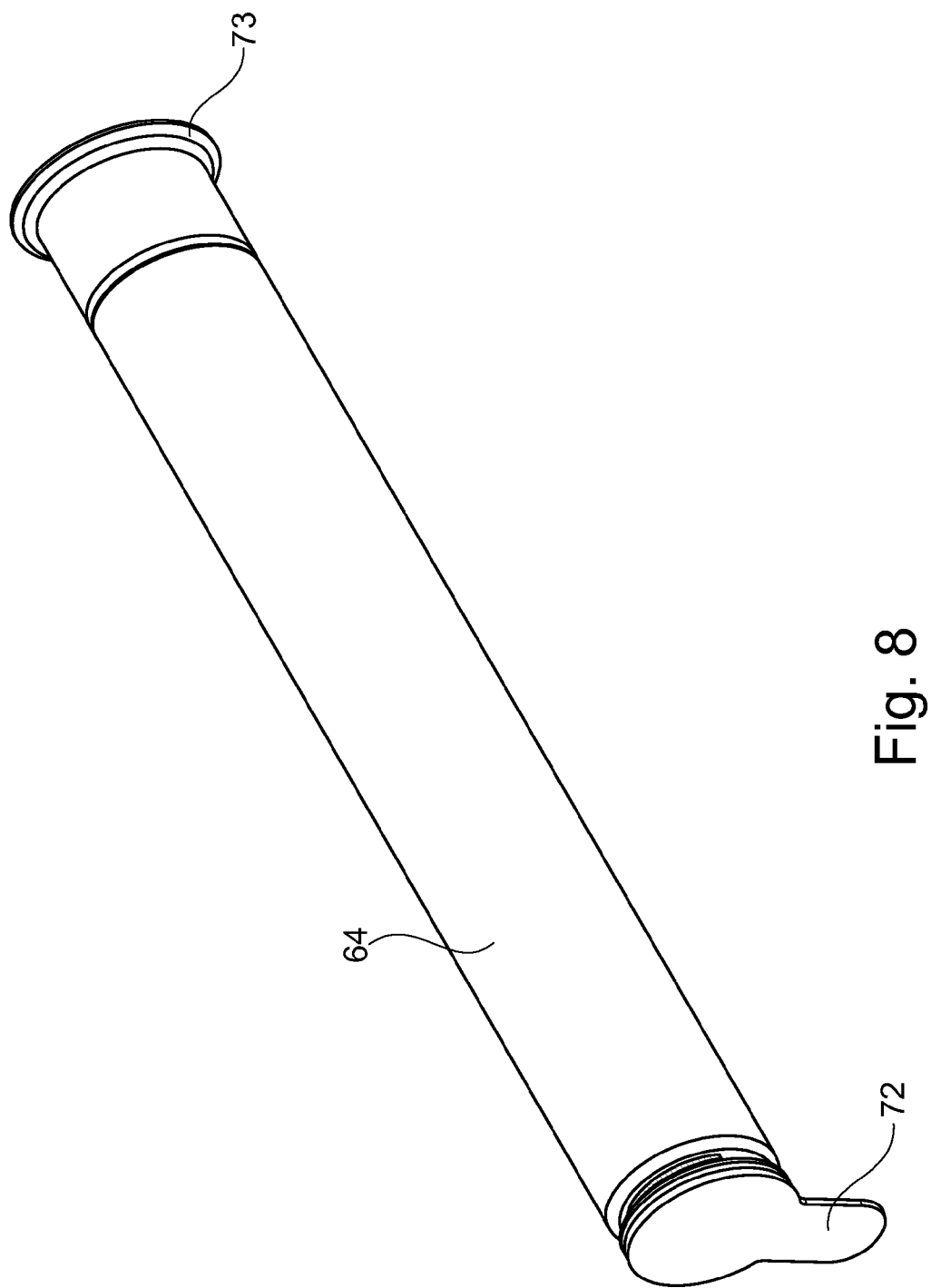
FIGS. 8-11 show a further embodiment, wherein the catheter sections are arranged in a telescopic fashion.

As shown in FIG. 5, an outer wall of the second catheter section 44 forms a handle, the tubular protective member 46 being arranged so that it extends out of the handle at the proximal end thereof. The tubular protective member 46 may form a flange at its proximal end, so as to facilitate a user's extraction of the first catheter section 42 and the tubular protective member 46 out of the handle/second catheter section 44. When extracted, the tubular protective member 46 and thus the first catheter section 42 surrounded thereby coextend with the handle or second catheter section 44, as illustrated in FIG. 6. A protrusion 47 at the distal end of the tubular protective member 46 releasably secures the tubular protective member 46 to the seal 50, see FIGS. 4, 6 and 7. The seal 50 may be designed so that it engages the proximal end portion of the second catheter section 44 by a snap action once the seal 50 and the tubular protective member 46 have reached the fully extracted position shown in FIG. 6. In the example shown in FIG. 4, the seal 50 has a groove 51 which, in the extracted position shown in FIGS. 6 and 7 engages a flange 45 at the proximal end of the second catheter section 44. Immediately prior to use of the catheter, the tubular protective member 46 is removed, so that the first catheter section 42 is exposed, as shown in FIG. 7.

Figure 9:
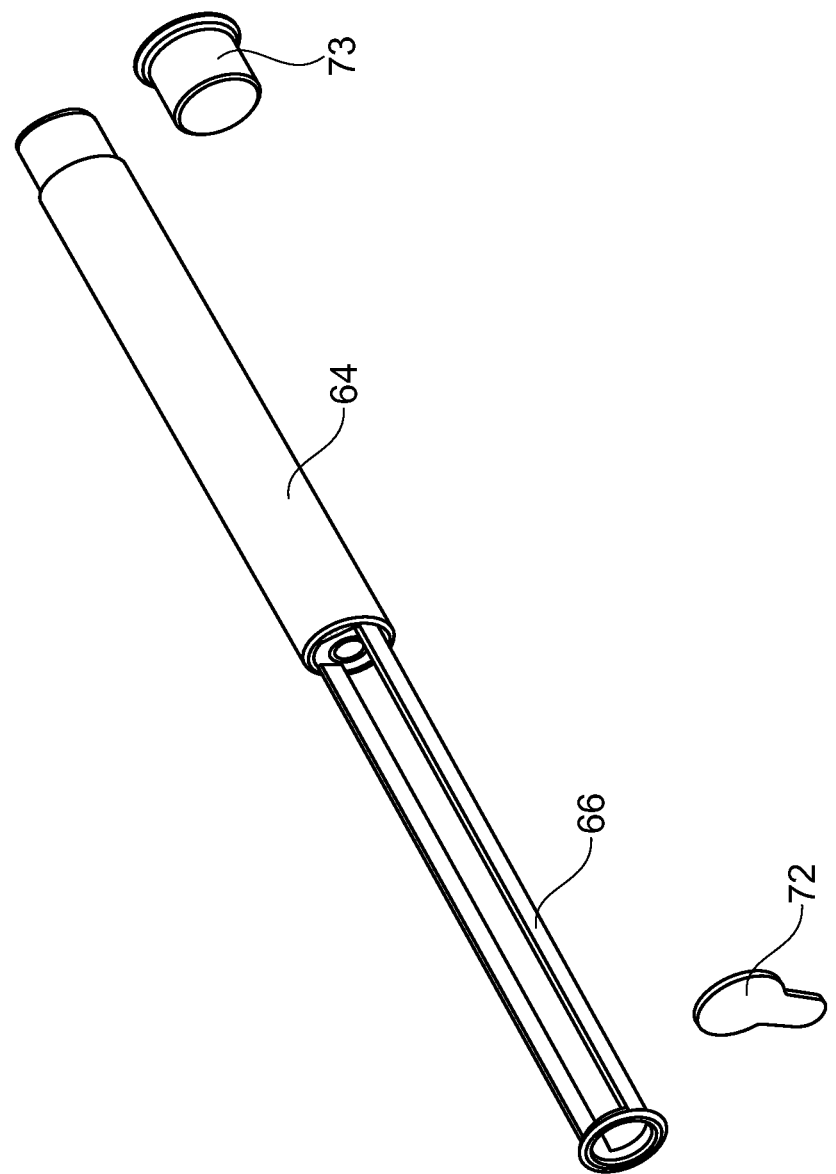
Figure 10:
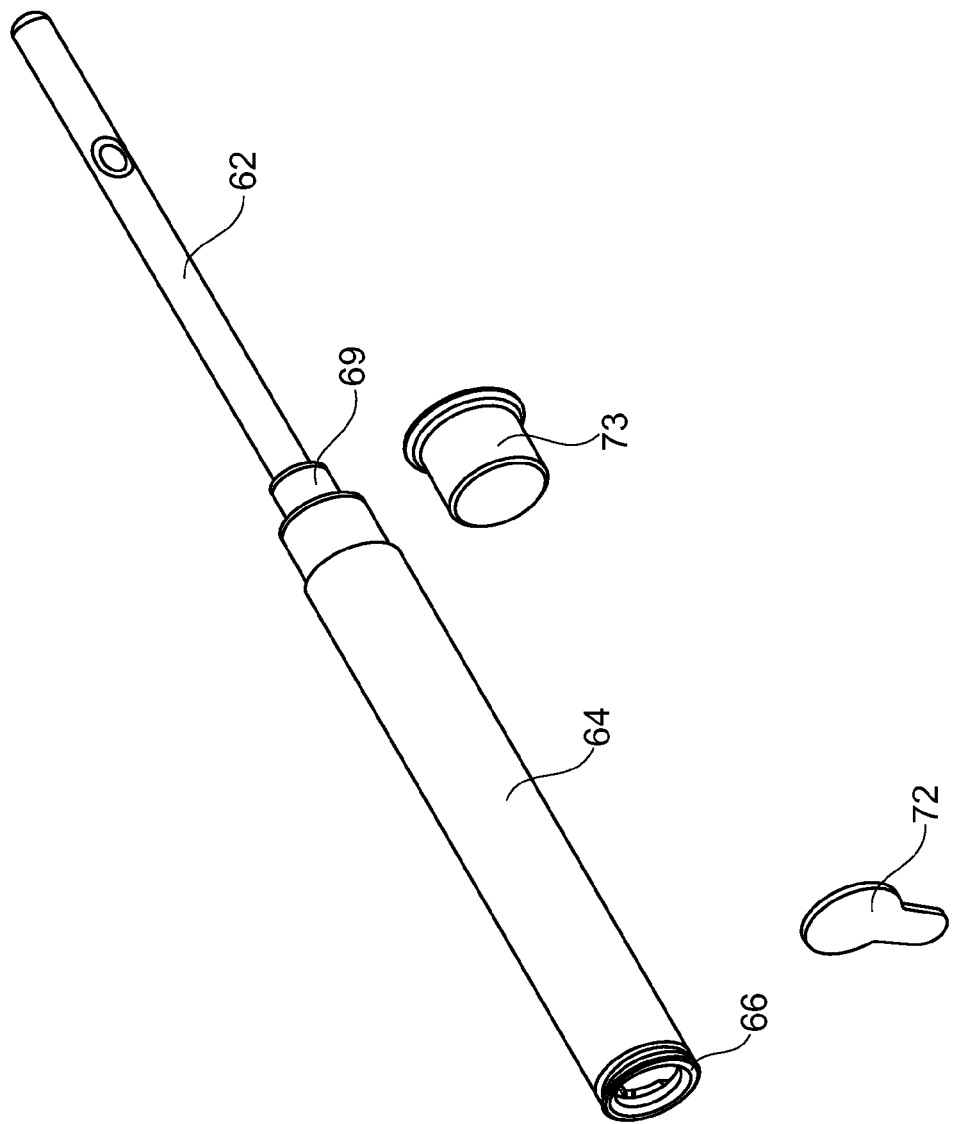
Figure 11:
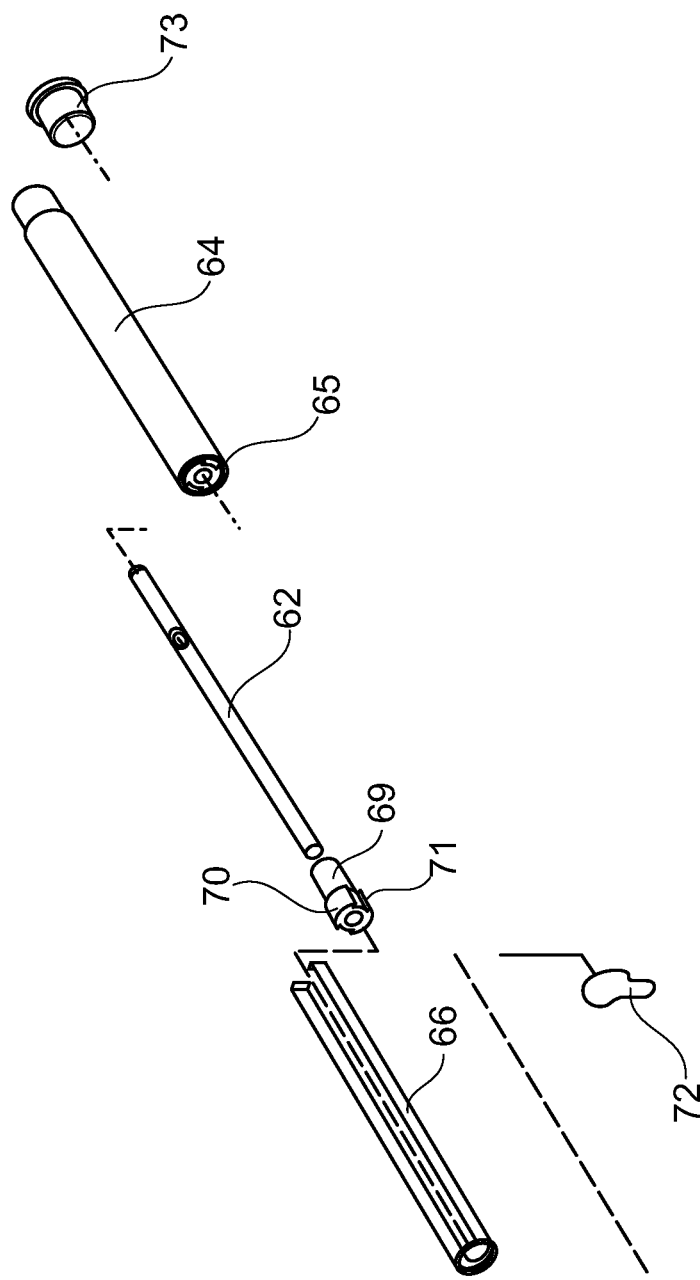

FIGS. 8-11 illustrate a further embodiment of a catheter kit, wherein the catheter sections are arranged in a telescopic fashion. As shown in the exploded view in FIG. 11, the kit comprises the following parts: a first catheter section 62, a second catheter section 64 with one or more inner flange portions 65, a guide member 66 with protrusions 67, a joint 69 with a collar portion 70 and slits 71 for the guide member 66, as well as a distal closure member 72 and a proximal closure member 73. The kit is stored and transported in the configuration shown in FIG. 8, wherein the second catheter section surrounds the first catheter section 62 and the guide member 66. Prior to use of the catheter, the distal closure member 72 is removed, and the guide member 66 is extracted, as shown in FIG. 9. The guide member 66 is extracted as far as possible, i.e. until the protrusions 67, due to their elasticity, engage respective grooves (not shown) provided in the slits 71 of the joint 69, see FIG. 11. The joint 69 is secured from sliding out of the second catheter section 64 by means of the inner flange portions 65 of the second catheter section 64. The proximal closure member 73 is also removed. Next, the guide member 66 is pushed back into the second catheter section 64. As the guide member engages the joint which is firmly connected to the distal end of the first catheter section, the joint 69 and the first catheter section 62 are pushed out of the distal end of the second catheter section 64 as the guide member 66 is pushed in the second catheter section 62. When the collar portion 70 of the joint 69 engages an inner flange or protrusion provided at the proximal end of the second catheter section 64, the kit is ready for use, and the first catheter section 62 may be introduced into the urethra of a human. A urine collection bag or other means for accumulating or conveying urine may be mounted to the proximal end of the second catheter section 64.

Figure 12:
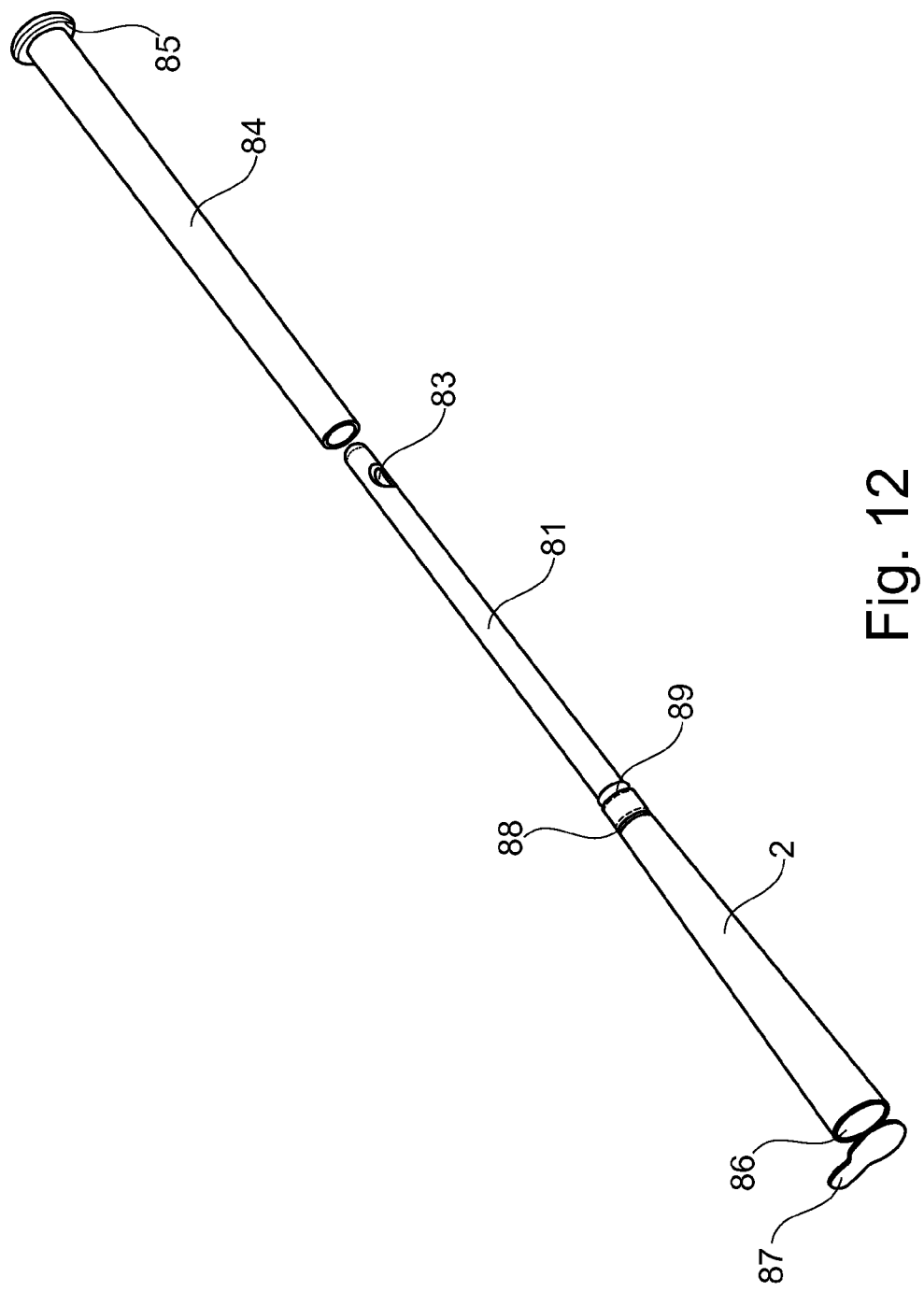
FIGS. 12 and 13 show yet a further embodiment, wherein the catheter sections are arranged in a coextending fashion.

The catheter shown in FIG. 12 has a first section 81 forming the proximal, insertable end of the catheter, and a second, proximal section 82 forming a handle part of the catheter. The first and second sections may have different shapes corresponding to their intended use. The first section is oblong and has an inlet opening 83 for draining urine from the bladder into an internal conduit extending through both part of the catheter, and the first section is slim when compared to the second part. The first section is covered by a tubular protective member 84 which is detachably attached to the outer surface of the catheter (in FIG. 1, the tubular protective member is removed and the catheter is ready for insertion into the urinary tract). The disclosed tubular protective member is cylindrical, and has an outward flange 85 supporting removal of the sleeve from the catheter. An internal conduit connects the inlet opening with the outlet opening 86 opposite the inlet opening in the second part. The outlet opening is covered by a foil 87 which is attached in a manner which allows peeling. A ribbed portion 88 gives the user a tactile indication of the transition between the first and the second section. The first and second sections are joined in a joint 89, e.g. by gluing or welding. Alternatively, the sections may be made in one piece.

Figure 13:
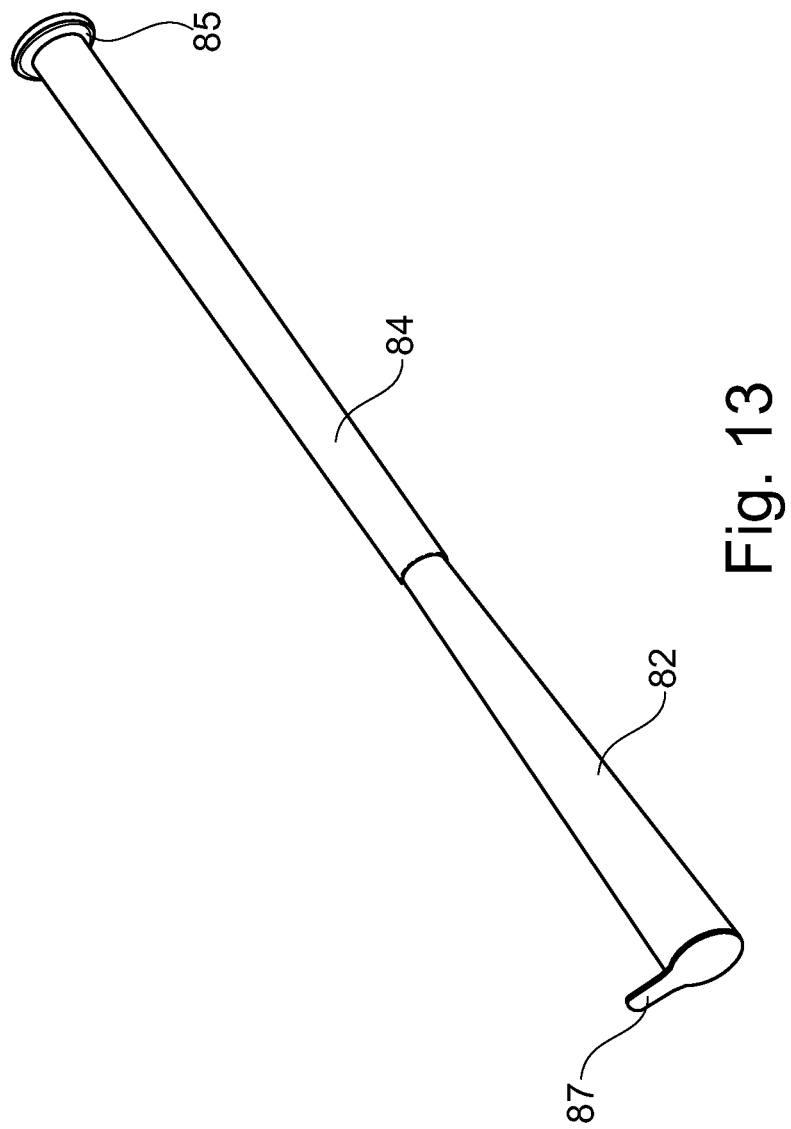

FIG. 13 shows the catheter of FIG. 12, wherein the tubular protective member 84 is attached to the catheter. The second section 82 is not covered by the tubular protective member. The tubular protective member fastens to the second part via an inwardly extending flange (not shown) engaging the ribbed portion 88.

Section II

Figure 14:
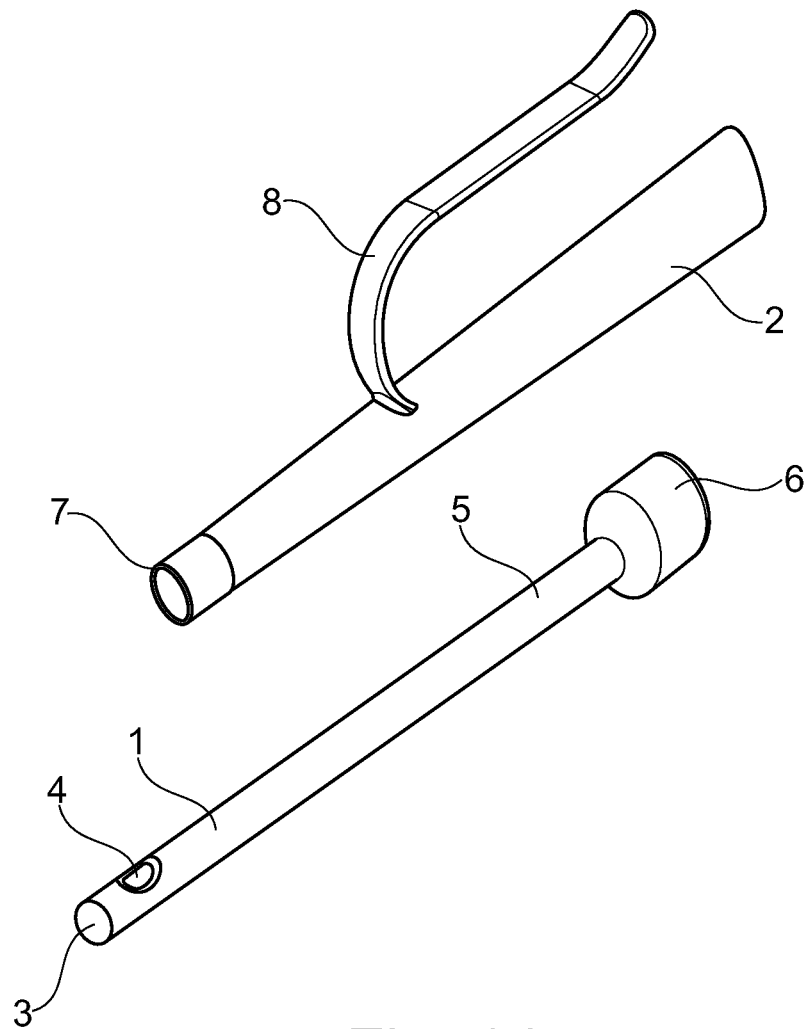
FIG. 14 shows a catheter kit according to the present invention.

Referring to FIG. 14, a catheter kit according to the present invention comprises a first elongate tubular catheter section 1 adapted for insertion into urethra or an artificial urinary canal and a second elongate tubular catheter section 2 adapted for manipulation of the catheter. At the proximal end 3, the tubular catheter section is provided with holes 4 enabling urine to drain into the tubular member. In order to protect the mucous membrane, the holes may preferably be provided on the side of the tubular member. Alternatively, a tubular member may be provided with a hole in the tip. It is important that the edge of the hole is rounded smoothly or that the material, for at least this part of the tubular member, is selected with the view not to cut or damage urethra, i.e. e.g. a soft resilient rubber material.

At the distal end 5, the tubular member is provided with connecting means 6 for connecting the catheter section to mating connecting means 7 of the second tubular catheter section. Preferably, the first and the second section is made from a thermoplastic elastomeric material, other thermoplastic materials, curable elastomeric materials, polyamide resins or elastomers or any mixture thereof, i.e. the group may comprise materials like, PVC, PU, PE, latex, Kraton™, PTFE (Teflon), FEP, Siloxane (silicone rubber), and/or FEP.

Figure 15:
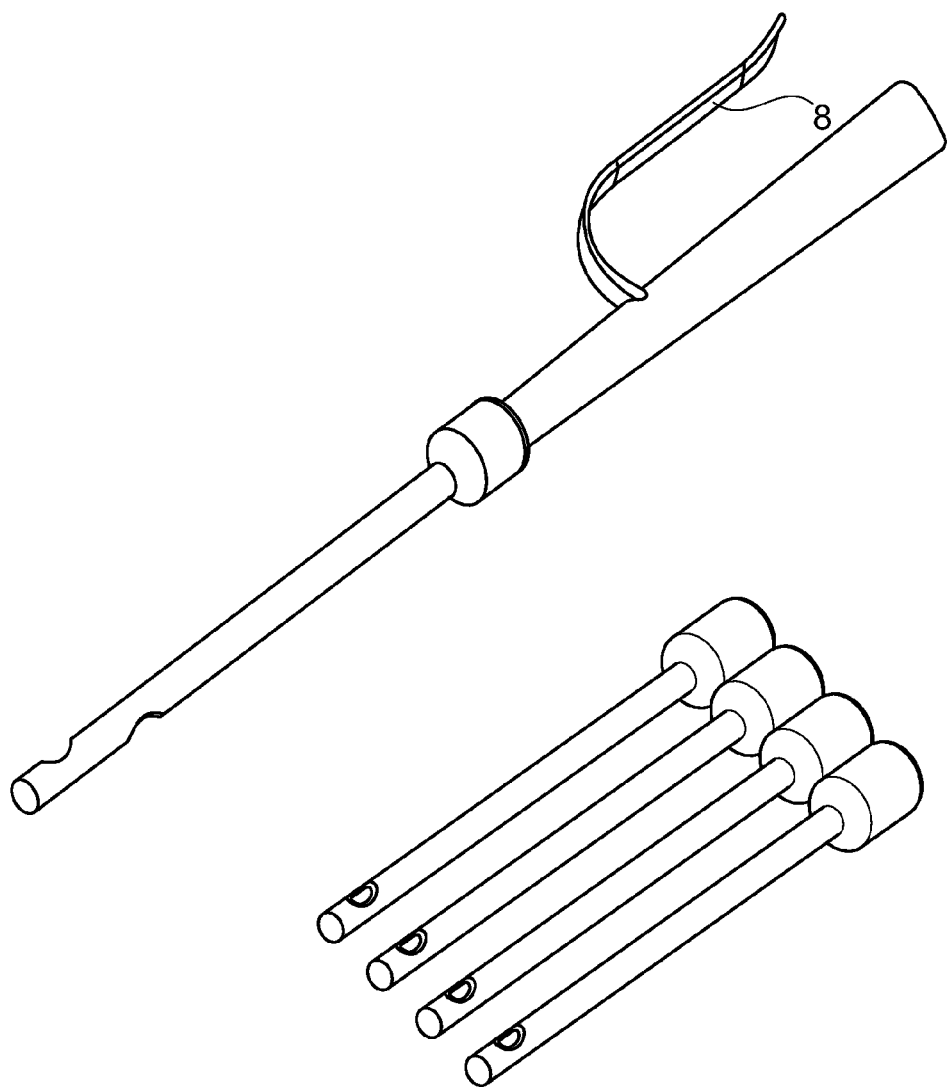
FIG. 15 shows the catheter kit of FIG. 14, assembled into a configuration for use.

FIG. 15 shows a view of the assembled catheter. The second catheter section is adapted to elongate the first catheter section so that the first and the second sections together form a rigid catheter having sufficient length to enable catheterisation. The rigidity of the first section should be sufficient to allow the section to be inserted into urethra without collapsing the section. The second section and the connection 6, 7—as shown in FIG. 14—between the second section and first section is provided with a rigidity that allows the insertion of the first section by manipulation of the second section. As seen in FIGS. 14 and 15, the catheter may preferably have gripping means 8 for easing a firm grip and manipulation of the catheter. In the embodiments of FIGS. 14 and 15, the kit may preferably be packed in a sterile package.

As indicated in FIG. 15, the kit may comprise one handle section and a number of catheter sections adapted for insertion or the kit may alternatively be packed in two packages—one containing a handle for multiple use and another separately steriliseable package containing one or more sections adapted for insertion and for one-time use. The sections may as an example be packed in manner similar to cartridges in a revolver or in a cartridge belt, i.e. interconnected to form a long row or tube of sections.

Figure 16:
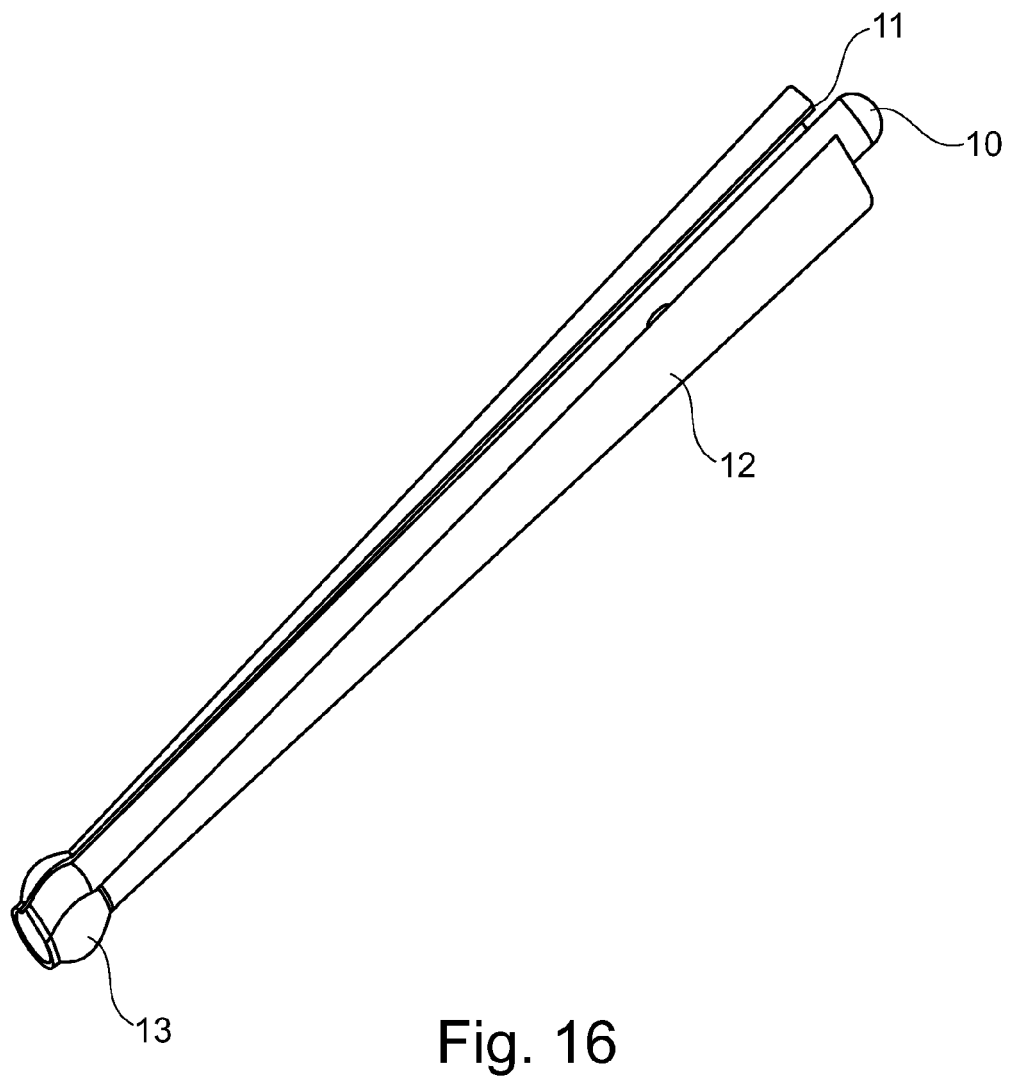
FIG. 16 shows a "Swiss-knife" embodiment of a catheter kit according to the present invention.

FIG. 16 shows a "Swiss-knife" embodiment of the catheter kit. The first catheter section 10 is folded into a slid 11 in the second catheter section 12. The first catheter sections being rotatably hinged to the second catheter section in the hinge connection 13.

Figure 17:
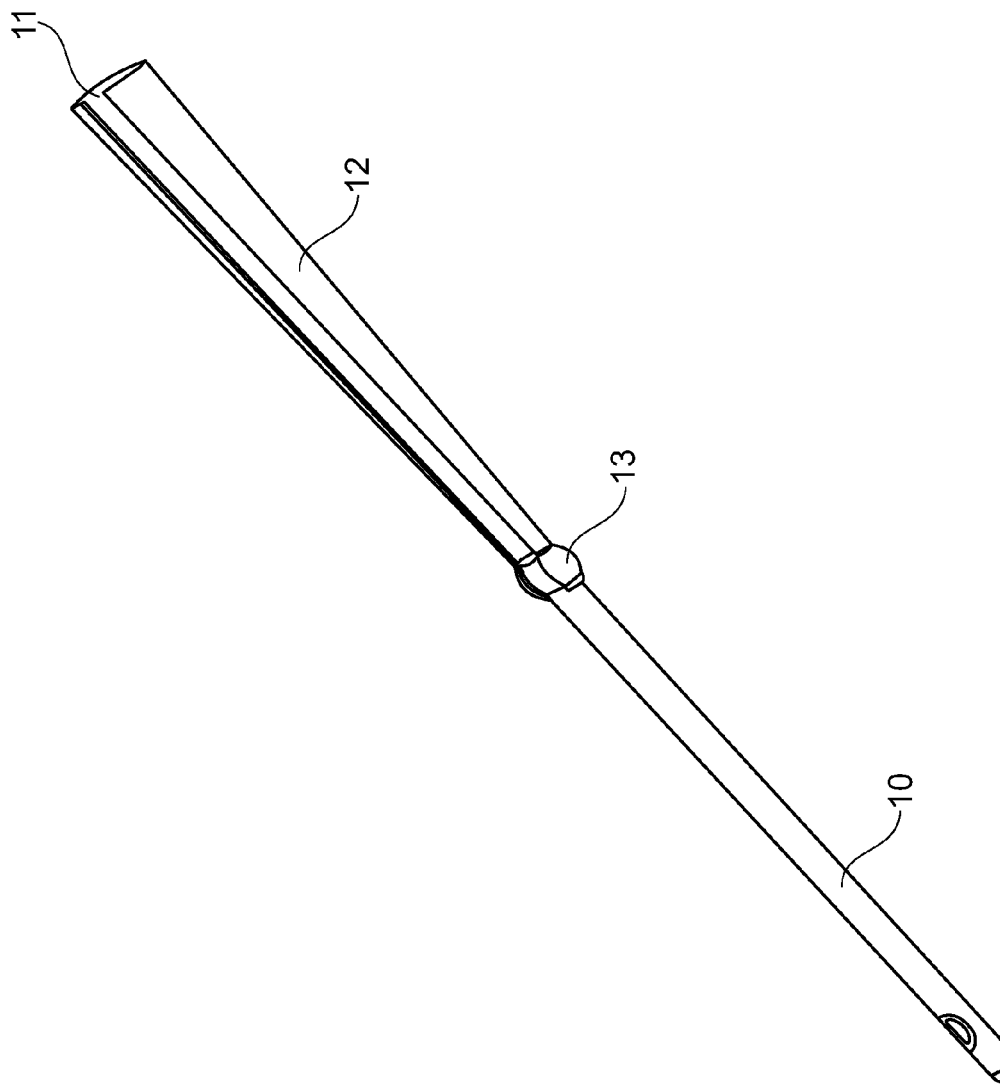
FIG. 17 shows the catheter kit of FIG. 16, unfolded and arranged in a configuration for use.

FIG. 17 shows the "Swiss-knife" embodiment unfolded. The slid 11 could as an example be covered with a thin latex foil, so as to seal the second catheter section. When the catheter is folded, the first catheter section will simply fold the latex foil radially inwardly into the second catheter section. As the catheter is unfolded, the elasticity and a slight pretension of the foil will lift the foil out of the slit and thereby provide free passage for urine to drain through the second catheter section. The latex foil is not shown in the FIGS. 16 and 17.

Figure 18:
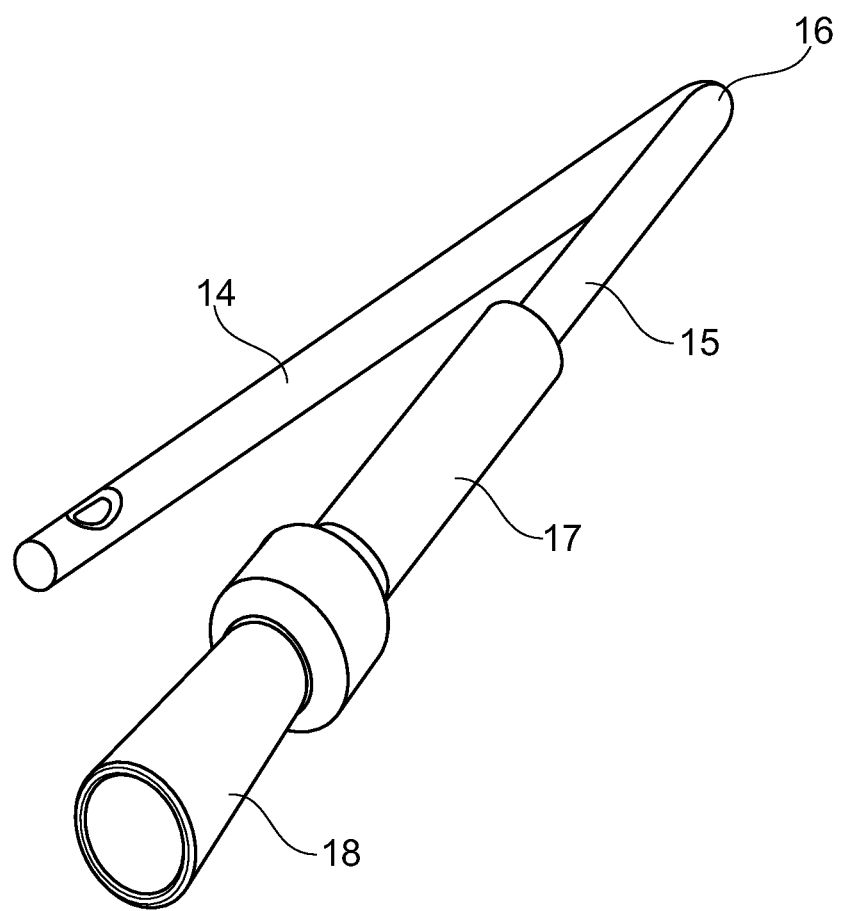
FIG. 18 shows a collapsed catheter provided with a reinforcement sleeve.

FIG. 18 shows an embodiment of the invention wherein a catheter is simply bend, whereby the catheter is divided into a first catheter section 14 and a second catheter section 15 by a collapsed catheter part 16. The catheter is provided with a reinforcement sleeve 17. The connector 18 enables connection of the catheter e.g. to a bag for collecting the urine.

Figure 19:
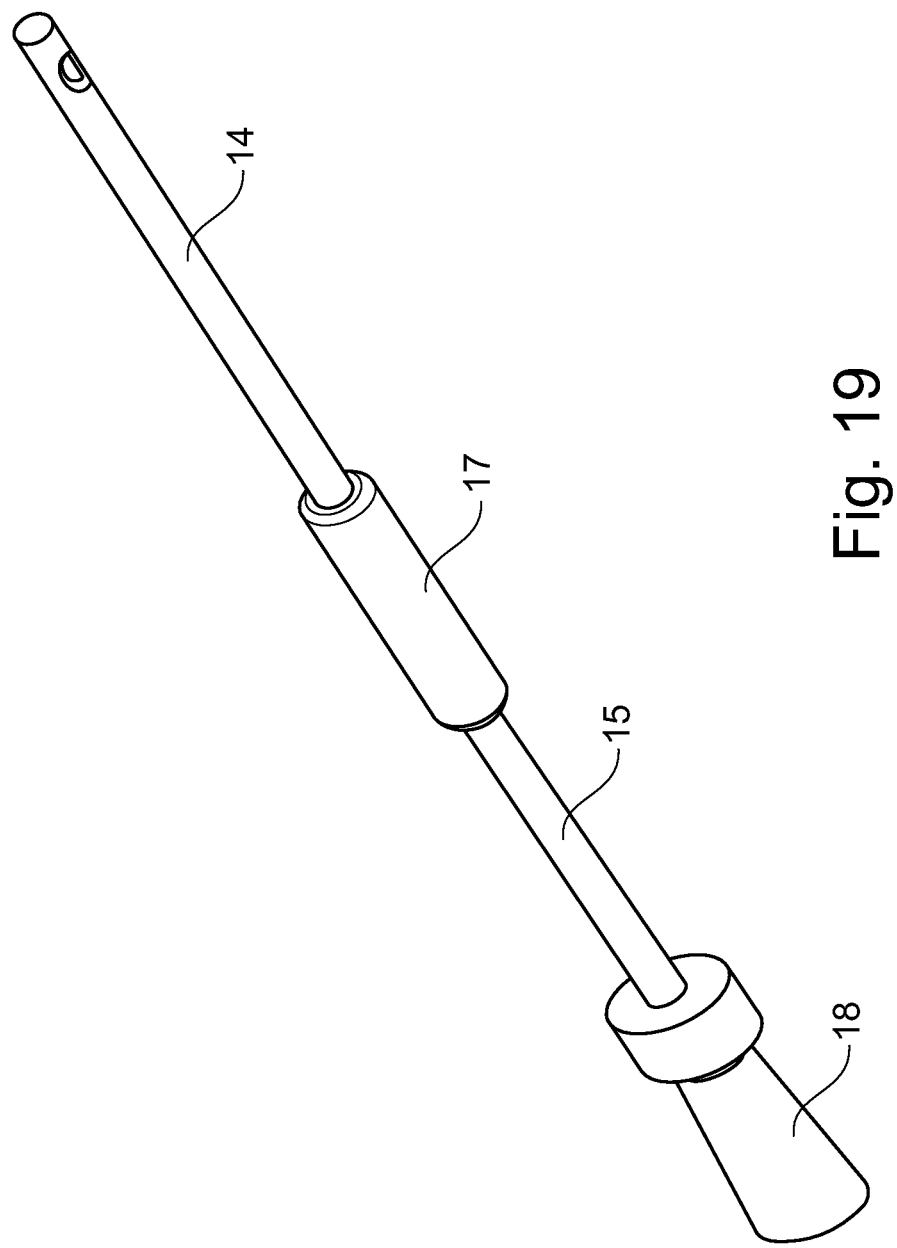
FIG. 19 shows the catheter kit of FIG. 18, unfolded and in a configuration for use.

FIG. 19 shows the unfolded catheter of FIG. 18. The sleeve 17 has now been displaced along the catheter so as now to support the catheter around the collapsed part 16 of the catheter.

Figure 20:
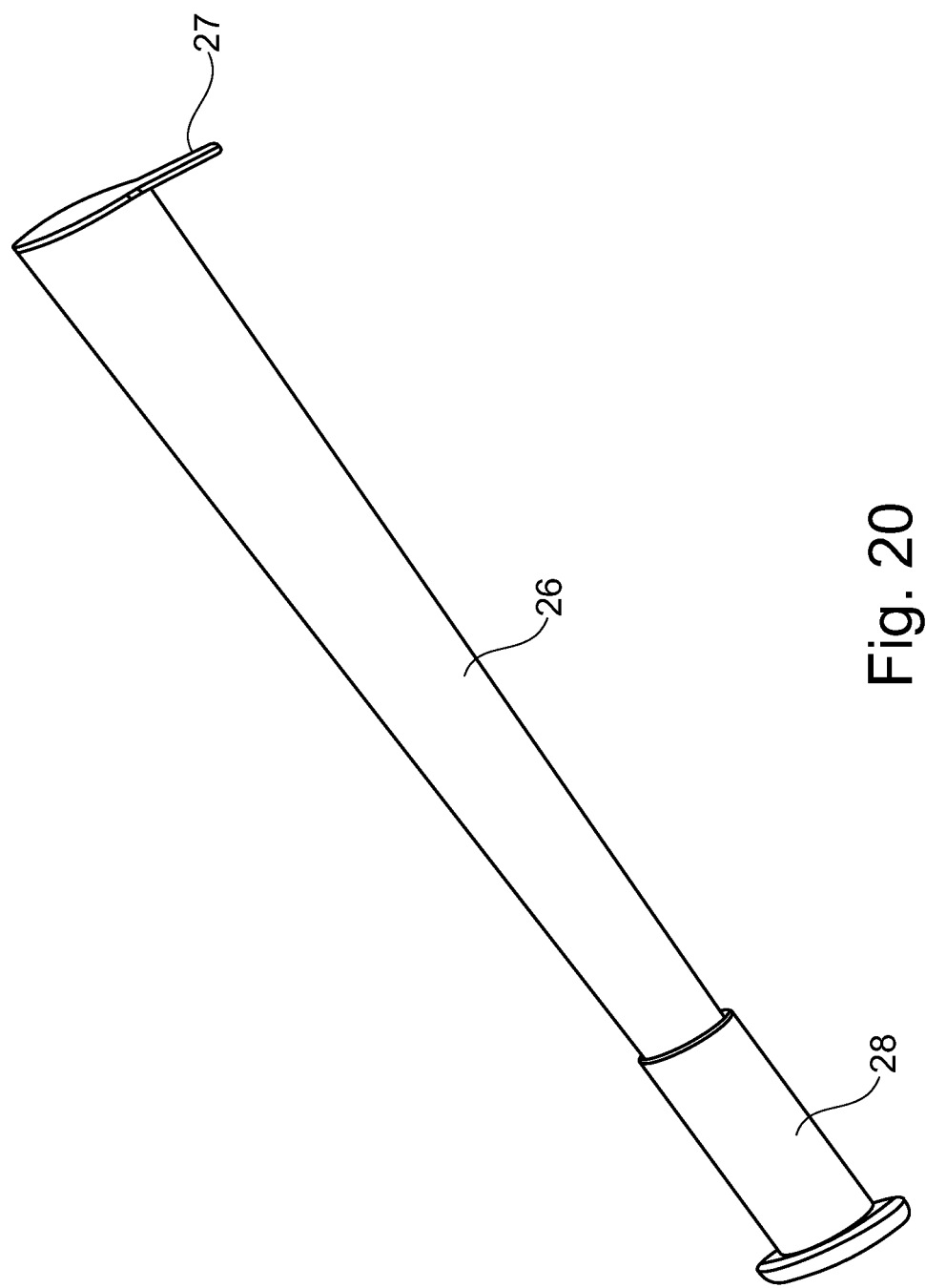
FIG. 20 shows a folded telescopic catheter kit.
Figure 21:
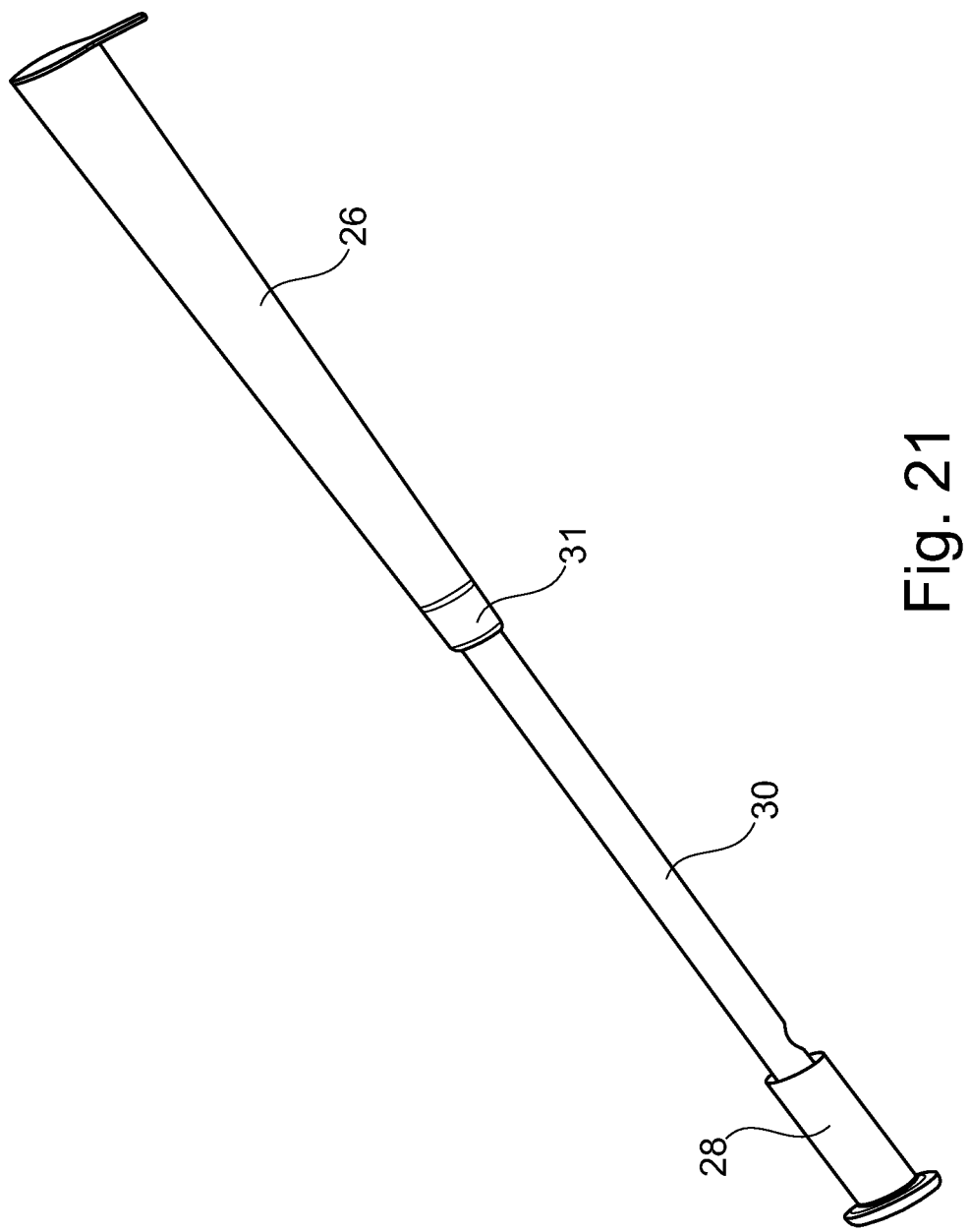
FIG. 21 shows the catheter kit of FIG. 20, in an extended configuration.

FIG. 20 shows an embodiment of the catheter kit wherein the first and the second catheter sections are connected telescopically. The first catheter section is sterilely packed inside the second catheter section 26. The second catheter section being sealed by a first sealing closure 27 and a second sealing closure 28. Prior to use, the first sealing closure is removed. If the first catheter section is provided with a hydrophilic surface layer, and if the catheter section is packed with a liquid swelling medium, the liquid medium may be emptied through the passage opened by the first sealing closure. As best seen in FIG. 21, the second sealing closure engages the first catheter section 30 for easy withdrawal of the first catheter section. When the first catheter section has been completely withdrawn, the distal part of the first catheter section engages the proximal end of the second catheter section in the connecting zone 31 and the second sealing closure easily disengages the first catheter section. The catheter is then in a configuration for use.

Figure 22:
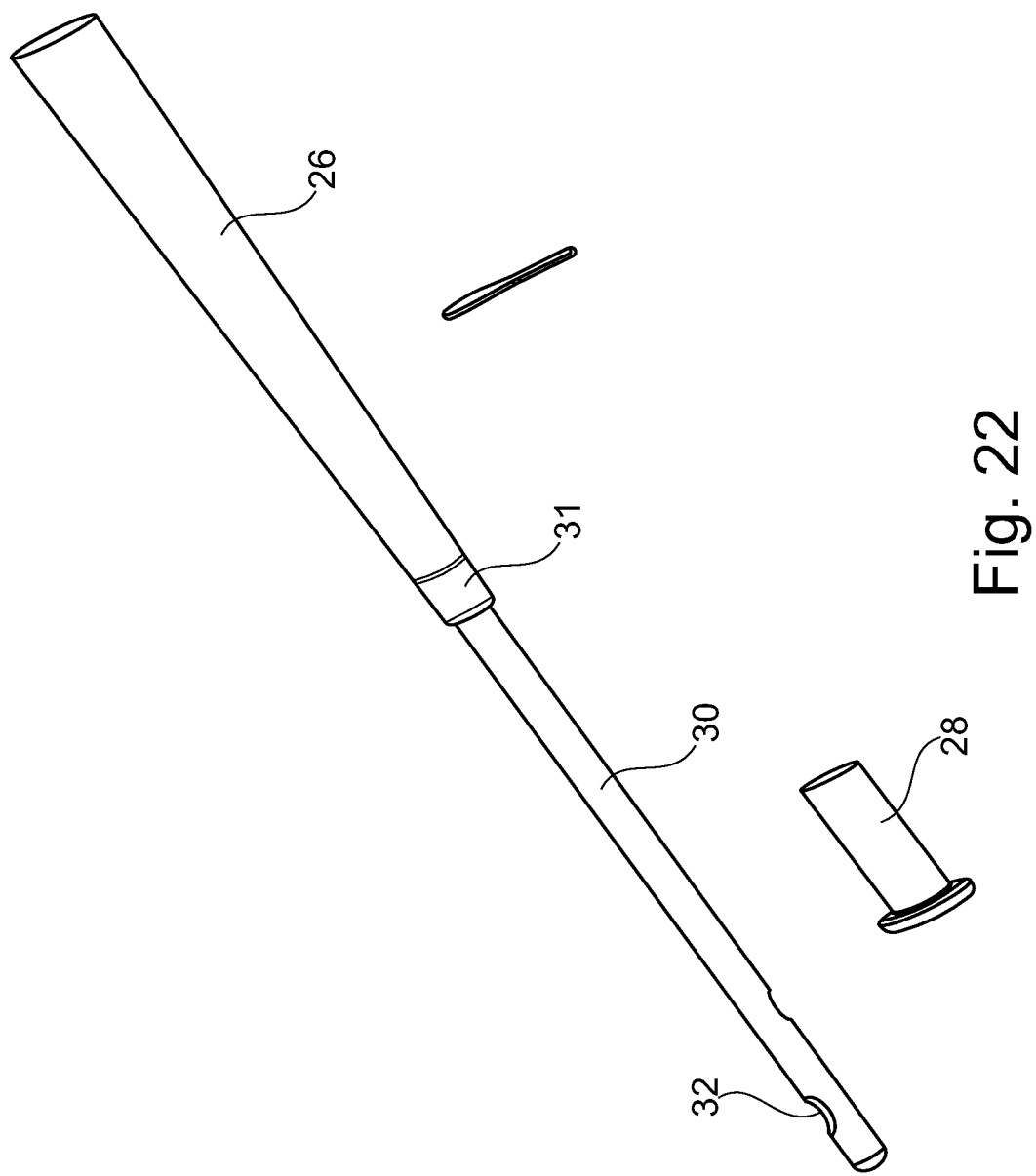
FIG. 22 shows the catheter kit of FIG. 20, unfolded and after withdrawal of the combined closure and withdrawal cap.
Figure 23:
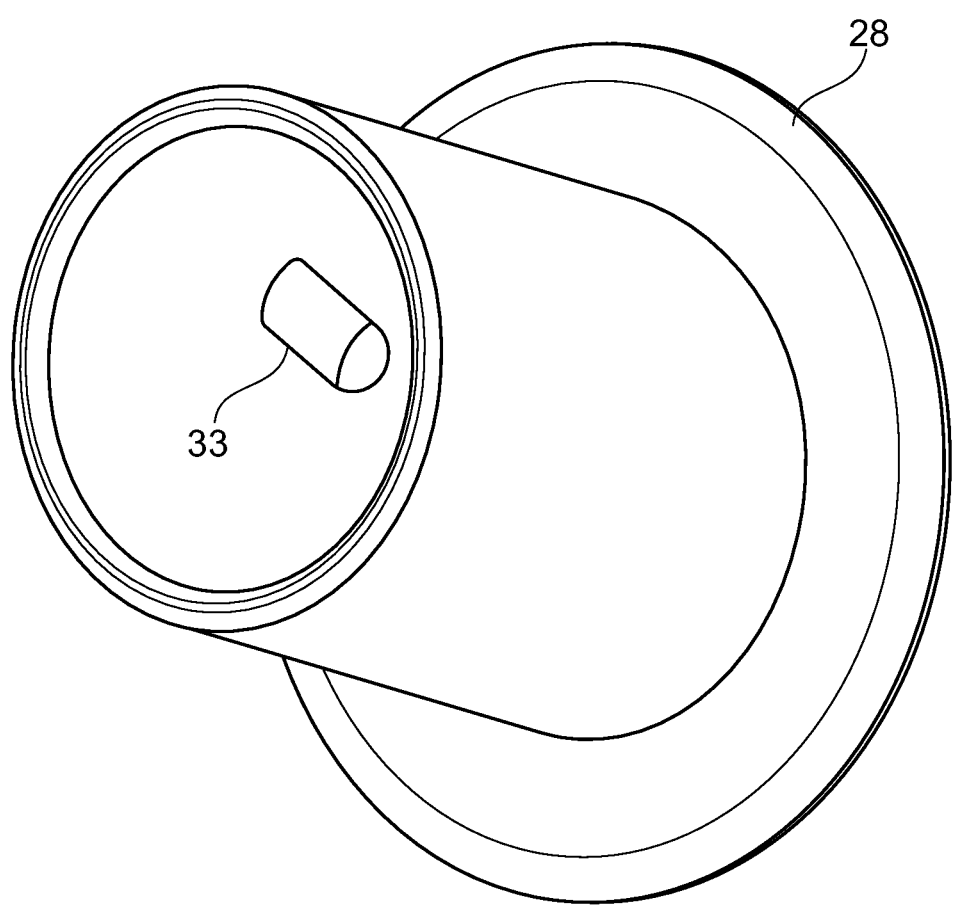
FIG. 23, shows a preferred embodiment of a combined closure and withdrawal cap for the kit shown in FIGS. 21 and 22.

FIG. 23 shows a preferred embodiment of the second sealing closure 28, wherein the closure is provided with internal and radially inwardly extending projections 33 adapted for engaging the hole 32 shown in FIG. 22.

Figure 24:
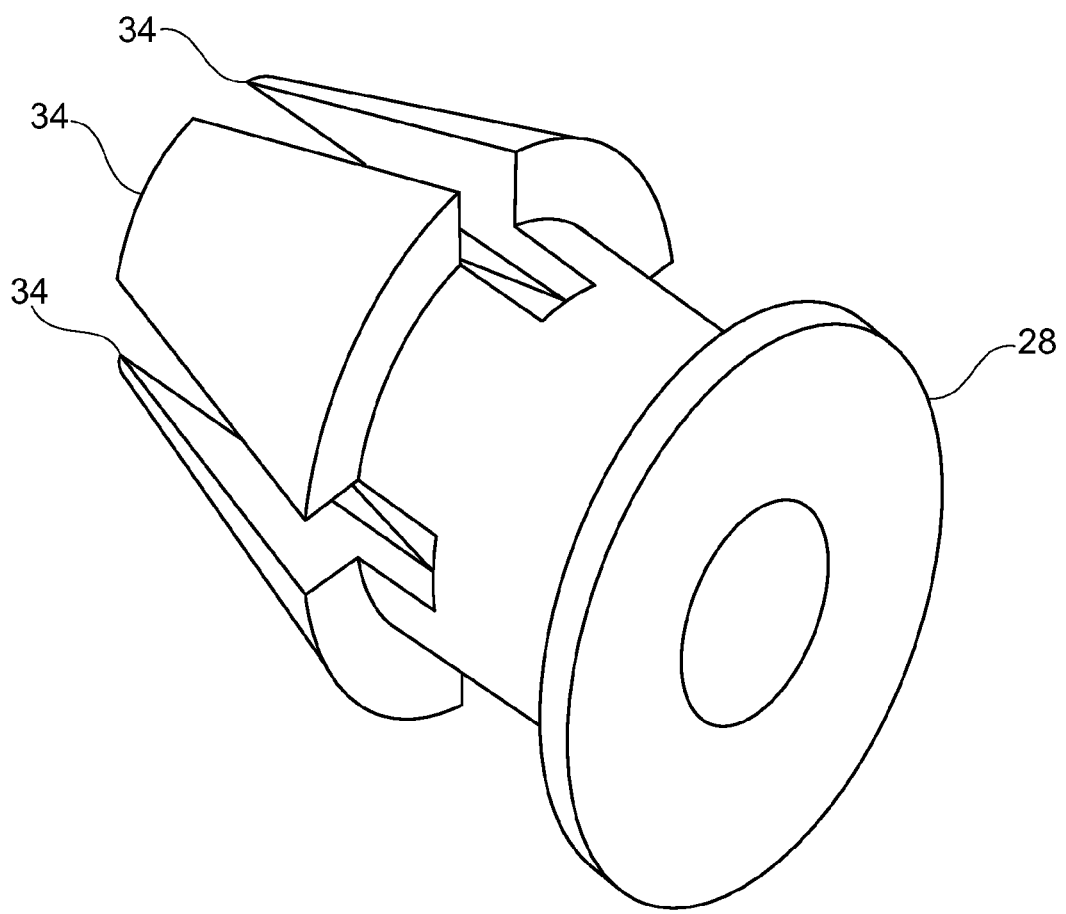
FIG. 24 shows yet another preferred embodiment of a combined closure and withdrawal cap for the kit shown in FIGS. 21 and 22.

FIG. 24 shows another embodiment of the second sealing closure 28, wherein flexible gripping flanges 34 softly grips the proximal (inserted) end of the first catheter section for easy withdrawal of the first catheter section from the second catheter section upon removal of the second sealing closure.

The telescopic embodiment of the catheter kit, disclosed in FIGS. 20-24, should preferably be provided so that the internal diameter of the second catheter section is slightly larger than the external diameter of the first catheter section. This is an advantage, e.g. in the case where the first catheter section is coated with a hydrophilic surface coating and in order not to scrape of the coating when sliding the first catheter section out of the second catheter section. On the other hand, it is an important aspect to provide a connecting zone wherein the first catheter section and the second catheter section firmly engages. Thereby, insertion and orientation of the first section is possible merely by manipulation of the second section and without the sections mutually sliding in the telescopic connection. It is furthermore important to assure that the first catheter section does not slip out of the second section in which case the first catheter section might disappear into the urethra. For this purpose, the distal end (opposite the inserted end) of the first catheter section may be provided with a radially outwardly extending flange disallowing the first catheter section to slip out of the second catheter section.

Figure 25:
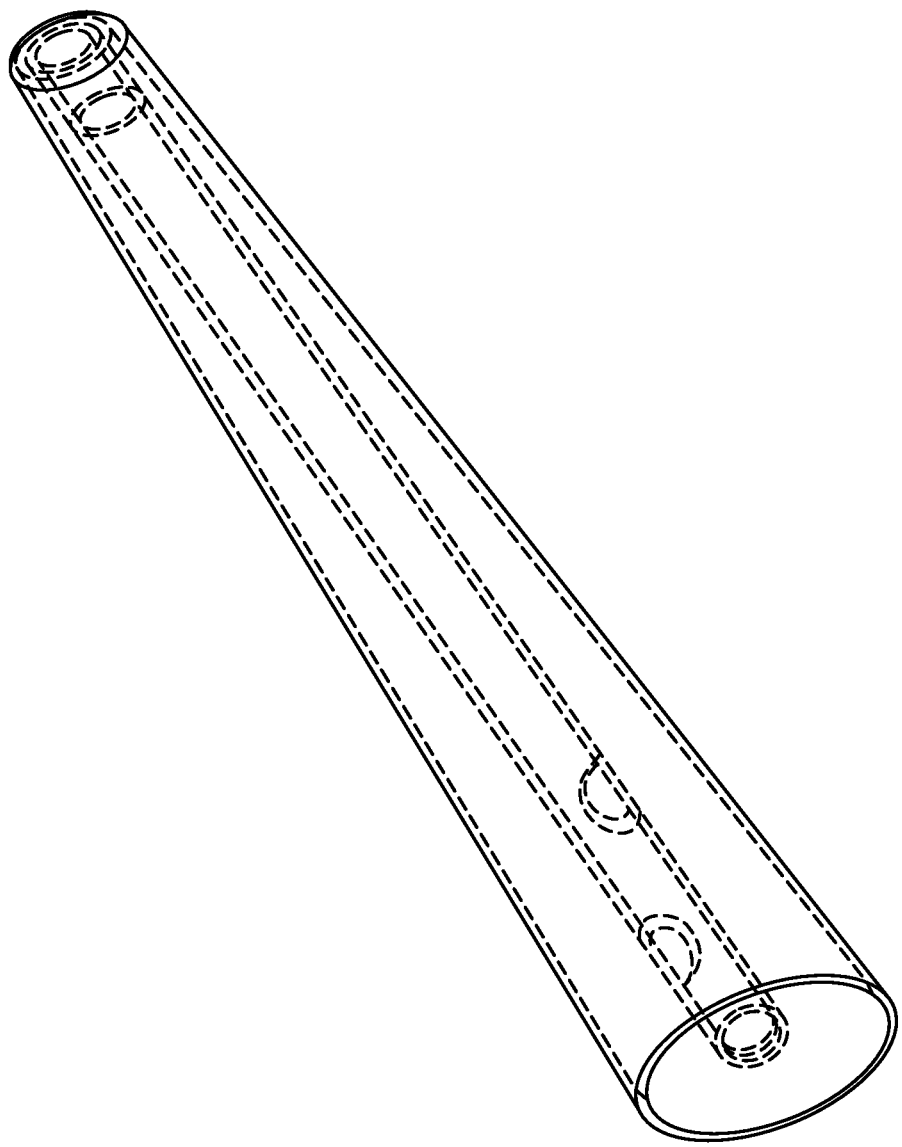
FIG. 25 shows a kit wherein a distal part of the catheter is curled over inserted part of the catheter so as to protect the inserted part of the catheter.

FIG. 25 shows an embodiment of the catheter kit wherein a second catheter section surrounding a first proximal catheter section can be turned inside out thereby the second catheter section protects the first catheter section prior to use. By provision of sealing foils or caps in both ends, the first catheter section may even be kept in a sterile condition inside the second section. Before use, the second catheter section is turned inside out by rolling or curling, whereby the catheter is brought into a configuration for use.

Figure 26:
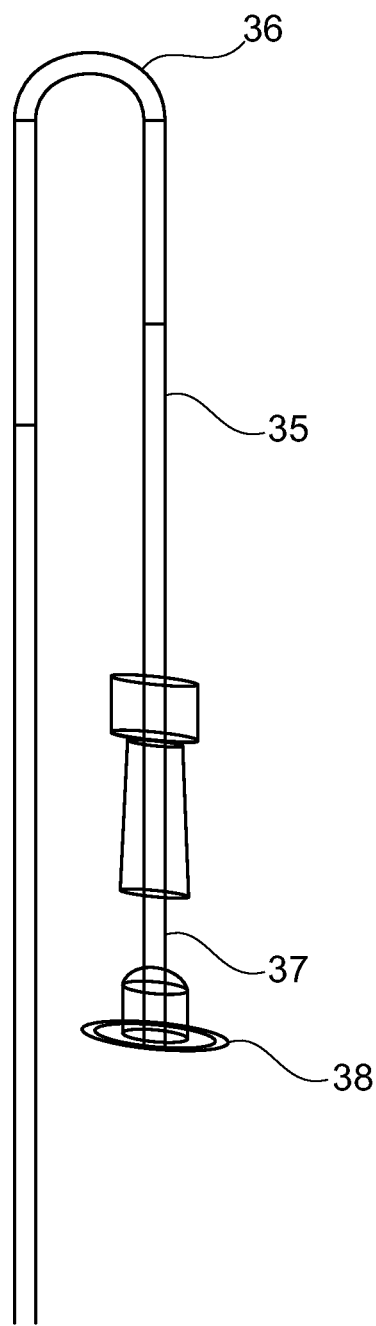
FIG. 26 shows a bendable catheter with a supporting member.

Referring to FIG. 26, one aspect of the present invention relates to a bendable catheter. The catheter is provided e.g. as a soft and flexible plastic hose 35, e.g. at least partly made from a thermoplastic elastomeric material, other thermoplastic materials, curable elastomeric materials, polyamide resins or elastomers or any mixture thereof, i.e. the group may comprise materials like, PVC, PU, PE, latex, Kraton™, PTFE (Teflon), FEP, Siloxane (silicone rubber), and/or FEP. The catheter is provided with a zone 36 allowing the catheter to bend. The zone may as an example be formed as a below shaped part of the catheter. If the catheter is relatively long and if a fairly large part of the catheter is to be inserted into the urethra, which is commonly the case for male users, it may be an advantage to provide a catheter which has a bendable zone which on the outside is so smooth that it may be inserted into the urethra. For this purpose the invention relates to a catheter having a supporting member inserted into at least the bendable zone. The supporting member may be a piece of an elongate helical spring provided with a conduit for draining the urine. The spring will easily provide support for the catheter so that the catheter does not collapse. The spring should be provided with an outer diameter as close to the inner diameter of the catheter hose as possible. As an example, the supporting member may be provided as a small piece of a spring, glued inside the catheter in the zone adapted to be bend. As another example, the supporting member may be provided as a longer spring 37, extending out through the opening of the catheter in the distal end (opposite the inserted end) of the catheter. The supporting member may thereby be removed prior to the insertion of the catheter into the urethra or even simultaneously with the insertion of the catheter into the urethra. For this purpose the supporting member may be provided with a handle 38.

Figure 27:
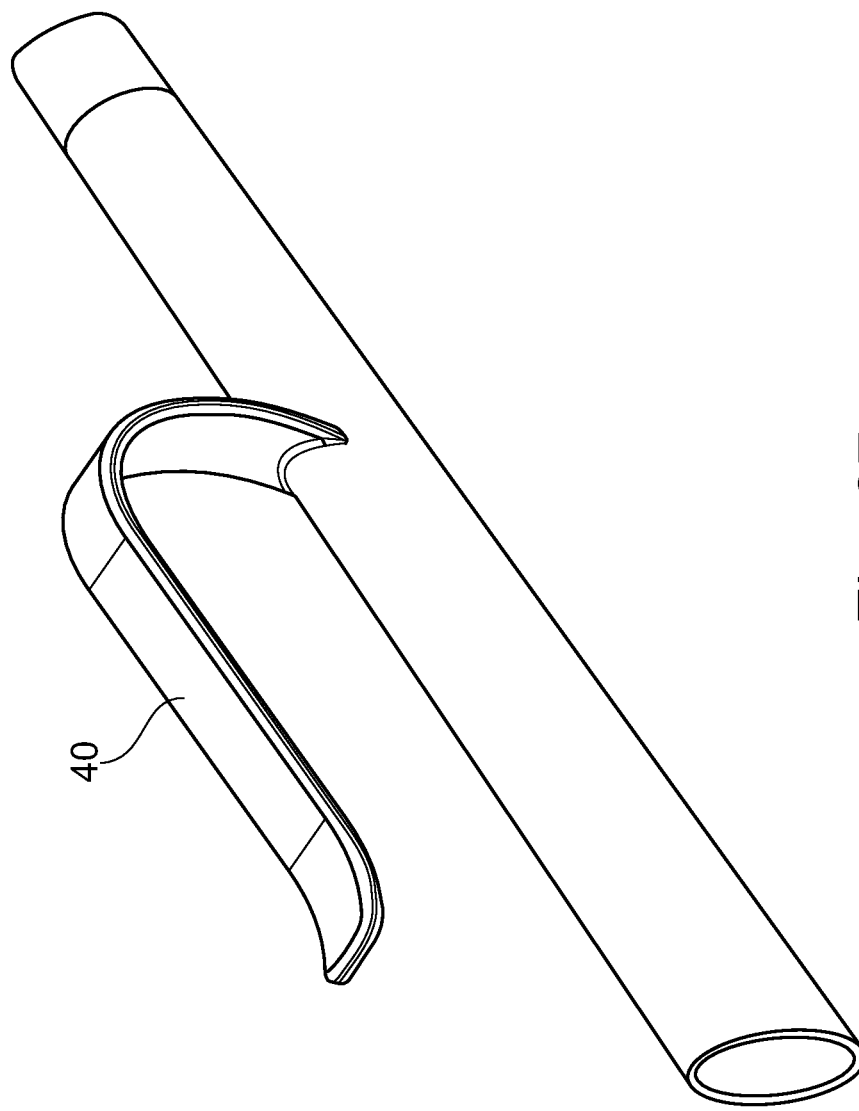
FIG. 27 shows a catheter part provided with gripping means for easing the handling of the catheter.

FIG. 27 shows a handle 40 for easy manipulation of the catheter. The handle may be highly appreciated not least for disabled users of the catheter e.g. for people having a reduced dexterity.

Figure 28:
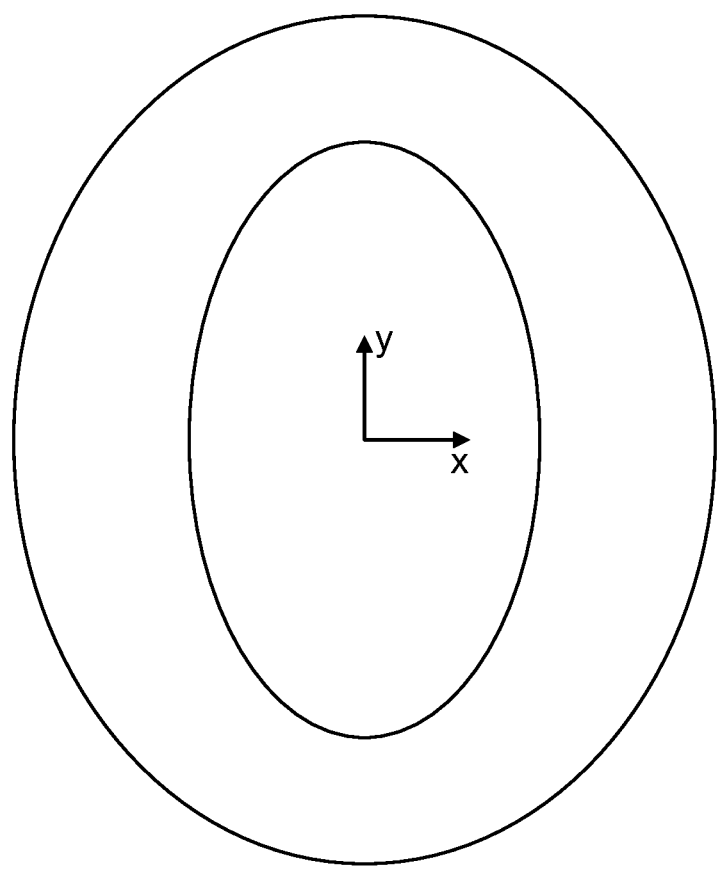
FIG. 28 shows a preferred cross-sectional shape of a catheter part adapted for insertion into the urethra.

FIG. 28 shows a preferred cross-sectional shape of the insertable part of the catheter. As the inserted part has an oval cross-sectional shape, the bending moment around the x-axis (indicated in FIG. 28) will be different from the bending moment around the y-axis. The relatively low bending moment around the y-axis will enhance the ability of the catheter to bend in one direction, and thereby easy the insertion of the catheter past prostate. The relatively high bending moment around the x-axis will enhance the general stiffness of the catheter thereby easing manipulation of the inserted part of the catheter from the part of the catheter not being inserted.

Figure 29:
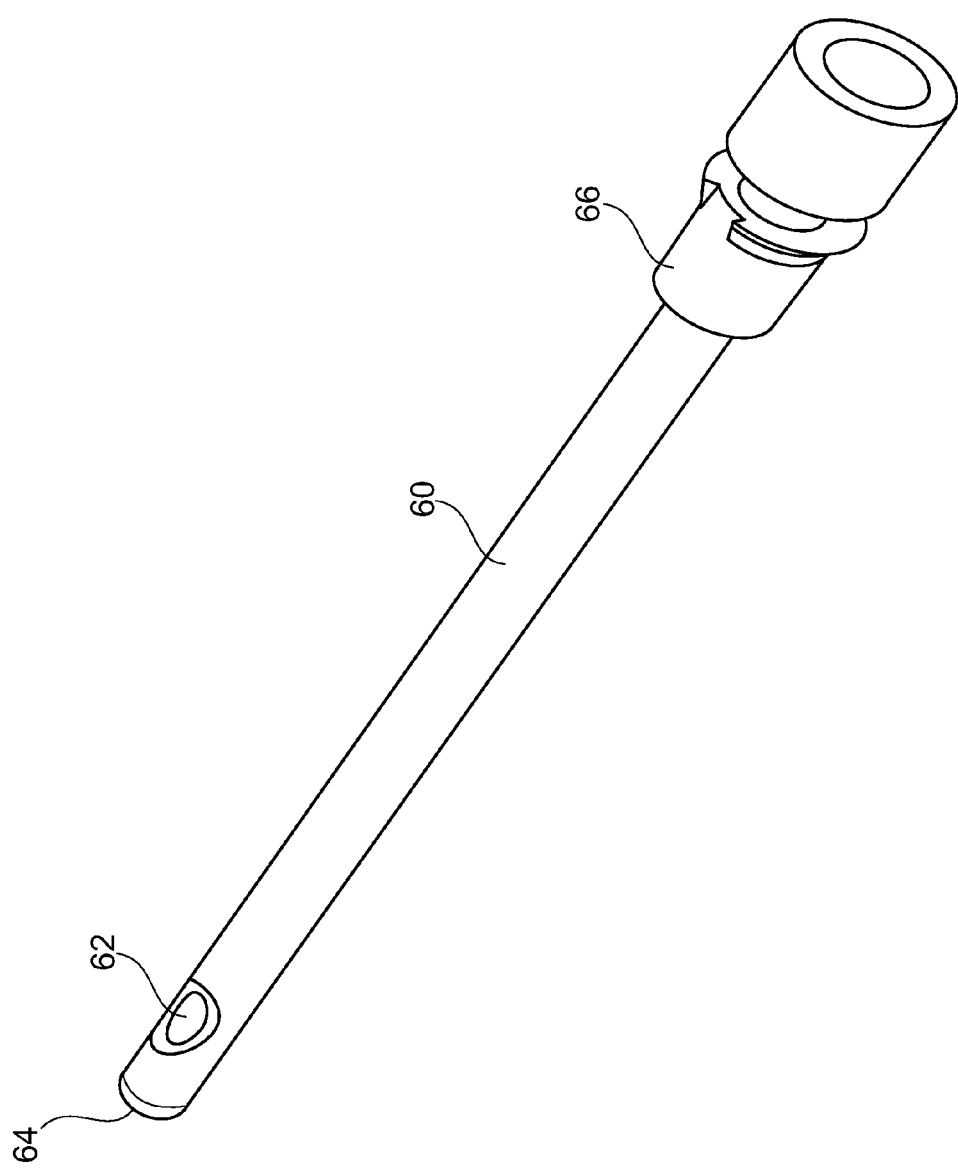
FIG. 29 shows a catheter produced by the method according to the invention.

FIG. 29 illustrates a catheter produced by the method according to the invention, the catheter having a proximal catheter section 60, at least part of which is adapted for insertion into the human urethra. The catheter section 60 forms one or more transversal passages 62, through which urine may flow once a proximal end of the catheter section 60 is inserted into the bladder. The section 60 is further provided with a rounded proximal tip 64 ensuring that the section can be inserted without damaging the membrane of the urethra. The catheter section 60 is formed in one single piece by injection moulding. The connector part 66 is formed integrally with the catheter section 60 during the same moulding operation. The connector part 66 may be adapted for connection of the section to a handle section or to a urine bag.

Figure 30:
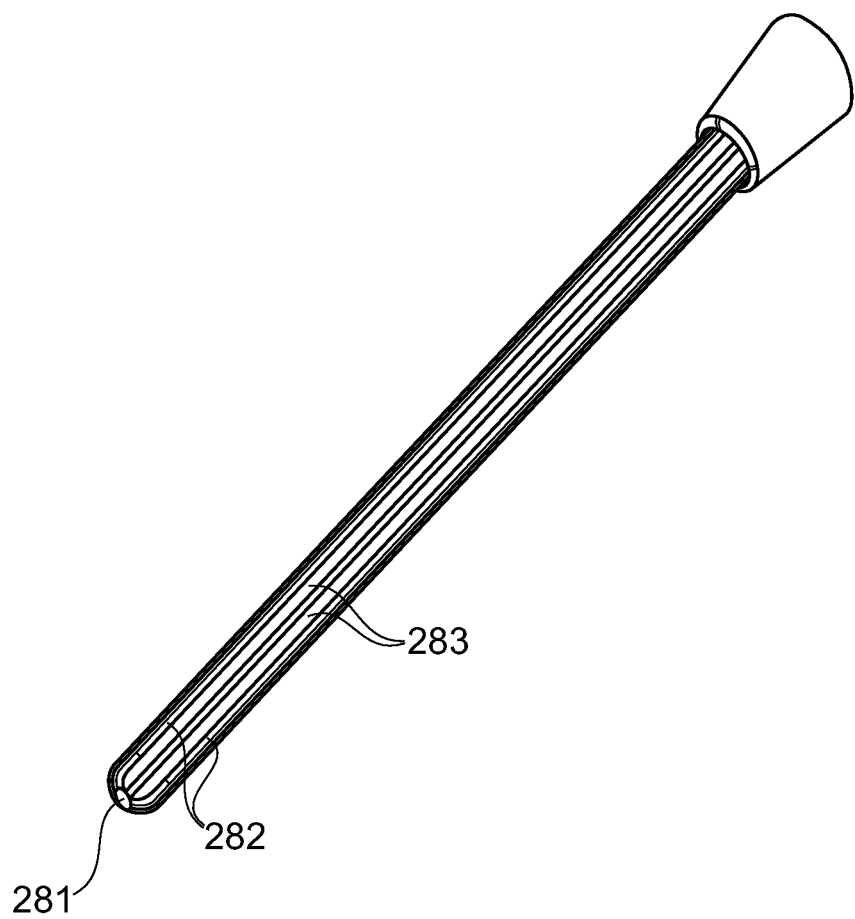
FIGS. 30, 31, and 32 shows an embodiment of a catheter section wherein the passage is defined between a solid kernel and the wall of a bodily channel such as the urethra.

FIG. 30 shows a perspective view of an embodiment of the catheter or a catheter section, comprising a solid kernel 281 with one or more vanes 282 extending radially from the kernel and along the entire length thereof. The vanes thus defines a number of draining passages 283 for draining urine between the kernel and a bodily draining passage, e.g. the urethra. The advantage of using a passage defined between a solid kernel and a wall of the urethra is, that the flow of bodily fluid cleans the urethra and thus reduces the risk of infection.

Figure 31:
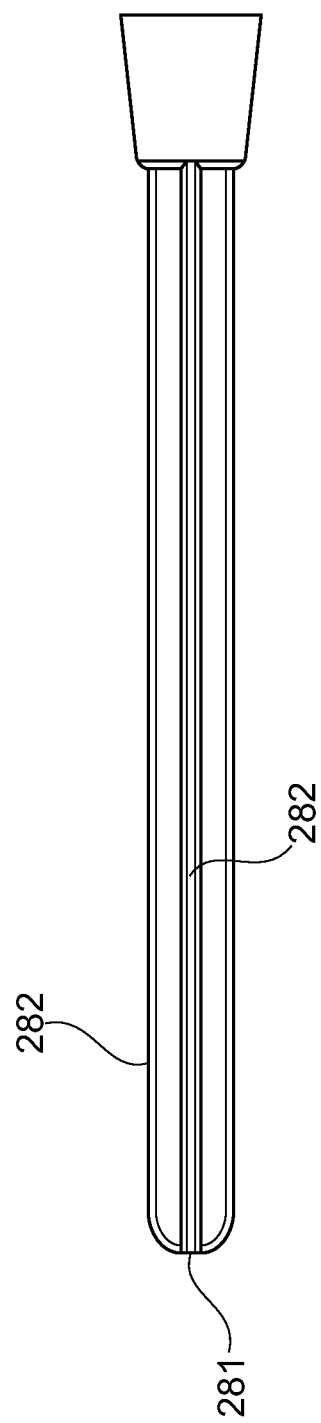
Figure 32:
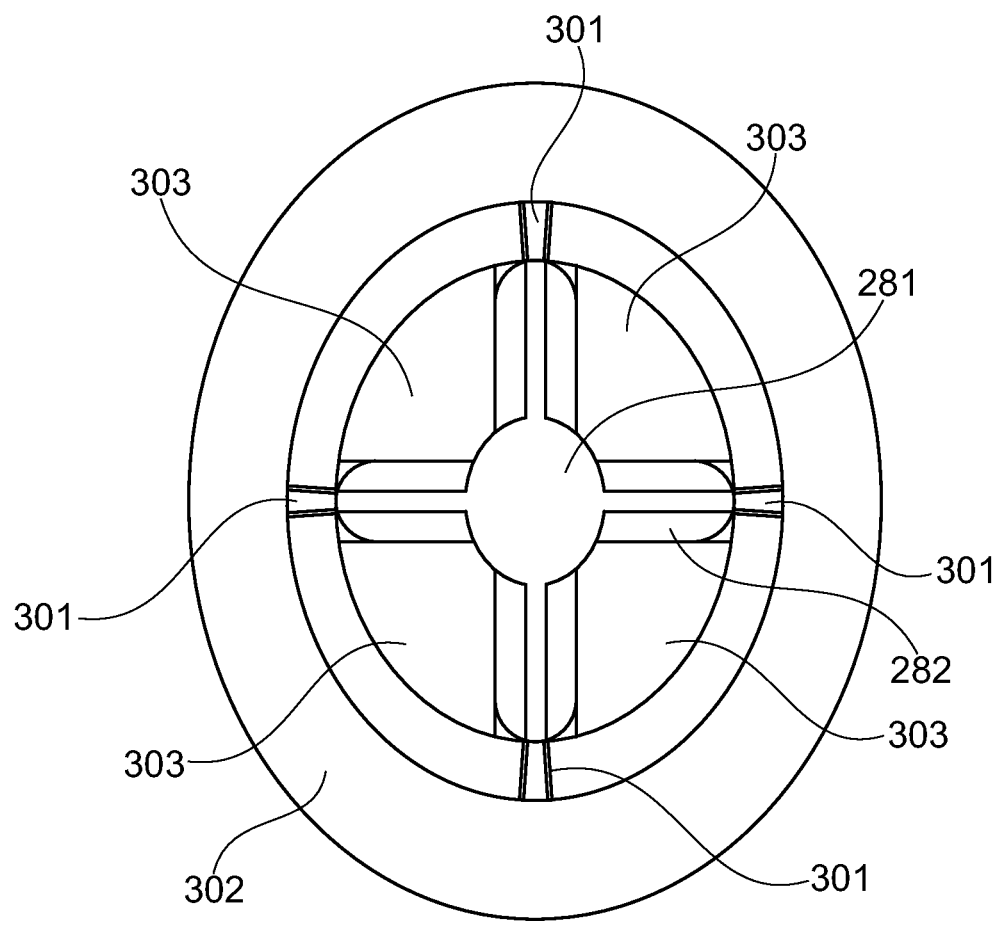

FIG. 31 shows a side view of the catheter section shown in FIG. 30. FIG. 32 shows a top view of the catheter shown in FIGS. 30 and 31. FIG. 32 shows the solid part 281 connected to a number of vanes 282. The vanes are again connected to a connector 302 via a number of spokes 301. A number of openings 303 are formed between the solid catheter part 281 and the connector 302. Except from the fact that the passage is defined between a solid core and the wall of the bodily channel and not inside a hollow tubular body, the catheter section of FIGS. 30-32 corresponds to the catheter section 42 of FIG. 4. The openings 303 correspond to the perforations of the catheter section of FIG. 4. The openings are provided in order to allow a friction reducing substance to drain out of the cavity 48 defined between the first and second catheter section, c.f. FIG. 4. The spokes 301 may preferably be formed with due regard to fluid dynamic aspects in order to allow fluid to drain passed the spokes without causing turbulence and without spreading the fluid. Spokes with a cross-sectional shape of a rhombus arranged with the longest leg parallel to the flow-direction, will support a substantially undisturbed flow passed the spokes.

What is claimed is:

1. A catheter insertable into a urethra to drain urine from a bladder, the catheter comprising:
   a tubular portion fixed to a connector with the catheter having a total catheter length measured between an end of the connector that is attachable to a drainage bag and an insertion end of the tubular portion that is insertable into the bladder, where the insertion end of the tubular portion has a closed and rounded tip;
   wherein the tubular portion has a bendable zone that is configured to allow the catheter to fold to a compact length that is less than the total catheter length, the compact length of the catheter characterized by the tubular portion having a bend in the bendable zone, and a passage is formed through a wall of the tubular portion between the bendable zone and the rounded tip of the insertion end; and
   a sleeve having a length defined by proximal and distal ends disposed on the tubular portion and slidable between first and second positions on the tubular portion, wherein at the first position the length of the sleeve is on a first side of the bendable zone to allow the catheter to fold to the compact length, and at the second position the sleeve is operable to support the tubular portion by removing the bend in the bendable zone, and thus align the connector axially with the insertion end of the tubular portion; and wherein, when the sleeve is in the second position, the catheter is insertable into the urethra to a position where the catheter is capable of draining urine from a bladder while the sleeve is in the second position removing the bend.

2. The catheter of claim 1, wherein the tubular portion has a first section located between the bendable zone and the insertion end of the tubular portion, and the bendable zone has a bending moment that is different from a bending moment of the first section of the tubular portion.

3. The catheter of claim 2, wherein the bending moment of the bendable zone is less than the bending moment of the first section of the tubular portion.

4. The catheter of claim 1, wherein the bendable zone is a bellows-shaped part of the tubular portion.

5. The catheter of claim 1, wherein the tubular portion has a first section located between the bendable zone and the insertion end of the tubular portion, and the bendable zone has a wall thickness that is less than a wall thickness of the first section of the tubular portion.

6. The catheter of claim 1, wherein the tubular portion has a first section located between the bendable zone and the insertion end and a second section located between the connector and the bendable zone, and the bendable zone has a bending moment that is lower than a bending moment of at least one of the first section and the second section of the tubular portion.

7. The catheter of claim 1, wherein the sleeve surrounds the tubular portion and is movable to the second position over the bendable zone of the tubular portion to support the catheter, remove the bend in the bendable zone, and align the connector axially with the insertion end of the tubular portion.

8. The catheter of claim 1, wherein an edge of the passage is treated to provide a rounded and curved edge.

9. The catheter of claim 1, wherein the tubular portion has a first section located between the bendable zone and the insertion end and a second section located between the connector and the bendable zone;
   wherein the sleeve is disposed on the second section and the first section is aligned straight between the bendable zone and the insertion end.

10. The catheter of claim 1, wherein the length of the sleeve is located between the bendable zone and the connector when at the first position.

11. A catheter insertable into a urethra to drain urine from a bladder, the catheter comprising:
    a tube with a first section located between a bendable zone of the tube and an insertion end of the tube, and a second section located extending away from the bendable zone on a side of the tube opposite from the first section;
    a connector fixed to the second section of the tube, with the catheter having a total catheter length measured between an end of the connector that is attachable to a drainage bag and the insertion end of the tube that is insertable into the bladder;
    wherein the tube is bent at the bendable zone to provide a folded catheter having a compact length that is less than the total catheter length, with the compact length characterized by locating the bendable zone at a first end portion of the folded catheter and locating both of the connector and the insertion end of the tube at a second end portion of the folded catheter opposite from the first end portion of the folded catheter; and
    a sleeve having a length defined by proximal and distal ends disposed on and slideable relative to the tube between first and second positions, wherein when the sleeve is at the first position the length of the sleeve is on a first side of the bendable zone allowing the catheter to be folded to the compact length, and when at the second position the sleeve is operable to remove a bend in the bendable zone and extend the catheter to the total catheter length with the connector aligned axially with the insertion end of the tube allowing for insertion into the urethra while the sleeve is in the second position.

12. The catheter of claim 11, wherein the sleeve surrounds the tube.

13. The catheter of claim 11, wherein the bendable zone has a bending moment that is less than a bending moment of the second section of the tube.

14. The catheter of claim 11, wherein the insertion end of the tube has a closed and rounded tip.

15. The catheter of claim 11, wherein a passage is formed through a wall of the tube between the bendable zone and the insertion end of the tube.

16. The catheter of claim 15, wherein an edge of the passage is treated to provide a rounded and curved edge.

17. The catheter of claim 11, wherein the length of the sleeve is located between the bendable zone and the connector when at the first position.

* * * * *